US010987317B2

(12) United States Patent
Cerione et al.

(10) Patent No.: US 10,987,317 B2
(45) Date of Patent: Apr. 27, 2021

(54) INHIBITION OF GLUTAMINASE C

(71) Applicant: Cornell University, Ithaca, NY (US)

(72) Inventors: Richard A. Cerione, Ithaca, NY (US); Jon W. Erickson, Freeville, NY (US); Kristin Wilson Cerione, Ithaca, NY (US); Jianbin Wang, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/741,635

(22) Filed: Jan. 13, 2020

(65) Prior Publication Data

US 2020/0206149 A1 Jul. 2, 2020

Related U.S. Application Data

(62) Division of application No. 13/259,533, filed as application No. PCT/US2010/028688 on Mar. 25, 2010, now Pat. No. 10,532,034.

(60) Provisional application No. 61/163,304, filed on Mar. 25, 2009.

(51) Int. Cl.
*A61K 31/473* (2006.01)
*A61K 31/00* (2006.01)
*C07D 471/04* (2006.01)
*C07D 249/12* (2006.01)
*C07D 239/62* (2006.01)
*C07D 277/06* (2006.01)
*C07D 221/18* (2006.01)
*A61K 31/4745* (2006.01)

(52) U.S. Cl.
CPC .......... *A61K 31/00* (2013.01); *A61K 31/4745* (2013.01); *C07D 221/18* (2013.01); *C07D 239/62* (2013.01); *C07D 249/12* (2013.01); *C07D 277/06* (2013.01); *C07D 471/04* (2013.01)

(58) Field of Classification Search
CPC .... A61K 31/473; A61K 31/4745; A61P 35/00
USPC .................................. 514/284, 285
See application file for complete search history.

(56) References Cited

U.S. PATENT DOCUMENTS

| 5,552,427 | A | 9/1996 | Matsutani et al. |
| 6,451,828 | B1 | 9/2002 | Newcomb et al. |
| 6,800,634 | B2 | 10/2004 | Sun et al. |
| 10,526,322 | B2 * | 1/2020 | Cerione ................... C12N 9/80 |
| 10,532,034 | B2 | 1/2020 | Cerione et al. |

FOREIGN PATENT DOCUMENTS

WO  WO 2007/120842  10/2007

OTHER PUBLICATIONS

ACS Registry No. 328084-72-6 (2001).
ACS Registry No. 367925-93-7 (2001).
ACS Registry No. 679822-57-2 (2004).
Aghaiypour et al., "Do Bacterial L-Asparaginases Utilize a Catalytic Triad Thr-Tyr-Glu?" *Biochim. Biophys. Acta*. 1550(2):117-128 (2001).
Aghaiypour et al., "Structural Basis for the Activity and Substrate Specificity of Enwinia chrysanthemi L-Asparaginase," *Biochemistry* 40(19):5655-5664 (2001).
Alonso et al., "Sensitisation of Ehrlich Ascitic Tumour Cells to Methotrexate by Inhibiting Glutaminase," *Anticancer Res*. 25(5):3315-3320 (2005).
Benavente & Jacobson, "Niacin Restriction Upregulates NADPH Oxidase and ROS in Human Keratinocytes," Author Manuscript published in *Free Radic. Biol. Med*. 44(4):527-527 (2008).
Benlloch et al., "Bcl-2 and Mn—SOD Anitsense Oligodeoxynucleotides and a Glutamine-Enriched Diet Facilitate Elimination of Highly Resistant B16 Melanoma Cells by Tumor Necrosis Factor-Alpha and Chemotherapy," J. Biol. Chem. 281(1):69-79 (2006).
Bhattacharya & Maity, "Localization of Phosphate Dependent Glutaminase in Ascites Fluid of Ovarian Cancer Patient," *Pathol. Oncol. Res*. 6(3):217-223 (2000).
Bhattacharya et al., "Effect of Purified Glutaminase From Human Ascites Fluid on Experimental Tumor Bearing Mice," *J Exp. Clin Cancer Res*. 20(4):599-607 (2001).
Bieganowski et al., "Eukaryotic NAD+ Synthetase Qns1 Contains an Essential, Obligate Intramolecular Thiol Glutamine Amidotransferase Domain Related to Nitrilase," J. Biol. Chem. 278(35):33049-33055 (2003).
Bui et al., "Retinal Function Loss after Monocarboxylate Transport Inhibition," *Invest. Ophthalmol. Vis. Sci*. 45(2):584-593 (2004).
Burbelo et al., "Altered Rho GTPase Signaling Pathways in Breast Cancer Cells," *Breast Cancer Res. Treat*. 84:43-48 (2004).
Buschdorf et al., "Brain-Specific BNIP-2-Homology Protein Caytaxin Relocalises Glutaminase to Neurite Terminals and Reduces Glutamate Levels," *J. Cell Sci*. 119:3337-3350 (2006).
Francis A. Carey, "Organic Chemistry 6th Ed." McGraw Hill. 2006, chapter 1, p. 9.
Carretero et al., "Mitochondrial Glutathione Depletion by Glutamine in Growing Tumor Cells," *Free Radic. Biol. Med*. 29(9):913-923 (2000).
Cammarano et al., "Dbl and the Rho GTPases Activate NFκB by IκB kinase (IKK)-Dependent and IKK-Independent Pathways," *J. Biol. Chem*. 276:25876-25882 (2001).
Campos et al., "Expression of Recombinant Human L-Glutaminase in *Escherichia Coli*: Polyclonal Antibodies Production and Immunological Analysis of Mouse Tissues," *Biochim. Biophys. Acta*. 1648(1-2):17-23 (2003).
Cappelletti et al., "Helicobacter Pyloril-Asparaginase: A Promising Chemotherapeutic Agent," *Biochem. Biophys. Res. Commun*. 377(4):1222-1226 (2008).

(Continued)

*Primary Examiner* — Charanjit Aulakh
(74) *Attorney, Agent, or Firm* — Troutman Pepper Hamilton Sanders LLP (Rochester)

(57) ABSTRACT

The present invention relates to a method of reducing the production of glutamate from glutamine by glutaminase C in a cell or tissue. The method involves inhibiting glutaminase C activity in the cell or tissue under conditions effective to reduce production of glutamate from glutamine. Compounds for carrying out this method are also disclosed.

5 Claims, 24 Drawing Sheets

Specification includes a Sequence Listing.

(56) References Cited

OTHER PUBLICATIONS

CAS Registry No. 296792-93-3 (2000).
CAS Registry No. 309719-68-4 (2000).
CAS Registry No. 312632-81-8 (2001).
CAS Registry No. 385375-94-0 (2002).
CAS Registry No. 406173-09-9 (2002).
Chakrabandhu et al., "Distinctive Molecular Signaling in Triple-Negative Breast Cancer Cell Death Triggered by Hexadecylphosphocholine (Miltefosine)," FEBS Lett. 582:4176-84 (2008).
Chambers et al., "Glutamine Metabolism Is Essential for Human Cytomegalovirus Infection," J. Virol. 84(4):1867-1873 (2010).
Chiarini et al., "Photoexcited Calphostin C Selectively Destroys Nuclear Lamin B1 in Neoplastic Human and Rat Cells—A Novel Mechanism of Action of a Photodynamic Tumor Therapy Agent," Biochim. Biophys. Acta. 1783(9):1642-1653.
Christofk et al., "Pyruvate Kinase M2 is a Phosphotyrosine-Binding Protein," Nature 452:181-186 (2008).
Clark et al., "Genomic Analysis of Metastasis Reveals an Essential Role for RhoC," Nature 406:532-535 (2000).
Conti et al., "Phosphate-Activated Glutaminase Pag Inhibitors Abolish Glutamate-Immunoreactivity in the Rat Cerebral Cortex," Soc. Neurosci. Abstr. 16(2):1188 (1990).
Curthoys, "Regulation of Glutaminase Activity and Glutamine Metabolism," Annu. Rev. Nutr. 15:133-159 (1995).
Dang, "MYC MicroRNAs and Glutamine Addiction in Cancers," Cell Cycle 8(20):3243-3245 (2009).
Dang et al., "MYC-Induced Cancer Cell Energy Metabolism and Therapeutic Opportunities," Clin. Cancer Res. 15(21):6479-6483 (2009).
De Melo et al., "Indole-3-Acetic Acid Increases Glutamine Utilization by High Peroxidase Activity-Presenting Leukocytes," Life Sci. 75(14):1713-1725 (2004).
Deberardinis et al., "Beyond Aerobic Glycolysis: Transformed Cells Can Engage in Glutamine Metabolism that Exceeds the Requirement for Protein and Nucleotide Synthesis," Proc. Nat'l. Acad. Sci. U.S.A. 104:19345-19350 (2007).
Deberardinis et al., "The Biology of Cancer: Metabolic Reprogramming Fuels Cell Growth and Proliferation," Cell Metab. 7:11-19 (2008).
Dhavala et al., "Expression, Purification and Crystallization of Helicobacter. Pylori L-Asparaginase," Acta. Cyrstallogr. Sect. F Struct. Biol. Cryst Commun. 64(Pt 8):740-742 (2008).
Dias & Cerione, "X-Ray Crystal Structures Reveal Two Activated States for RhoC," Biochemistry 46:6547-58 (2007).
Donadio et al., "Antisense Glutaminse Inhibition Modifies the O-GlcNAc Pattern and Flux Through the Hexosamine Pathway in Breast Cancer Cells," J. Cell. Biochem. 103(3):800-811 (2008).
Dos Santos et al., "Metabolism of the Microregions of Human Breast Cancer," Cancer Lett. 216(2):243-248 (2004).
Elgadi et al., "Cloning and Analysis of Unique Human Glutaminase Isoforms Generated by Tissue-Specific Alternative Splicing," Physiol. Genomics 1(2):51-62 (1999).
Erdmann et al. "In Vitro Glutaminase Regulation and Mechanisms of Glutamate Generation in HIV-1-Infected Macrophage," J. Neurochem. 109:551-561 (2009).
Erickson et al., "Structural Elements, Mechanism, and Evolutionary Convergence of Rho Protein-Guanine Nucleotide Exchange Factor Complexes," Biochemistry 43:837-842 (2004).
Estrada et al., "A Novel Approach for the Virtual Screening and Rational Design of Anticancer Compounds," J. Med. Chem. 43:1978 (2000).
Etienne-Manneville et al., "Rho GTPases in Cell Biology," Nature 420:629-635 (2002).
Ewart et al. "Rapid Activation of Hepatic Glutaminase in Rats Fed on a Single High-protein Meal," Biochem. J. 293:399-344 (1993).
Fiatte et al., "Expression of PPAR-Gamma Is Reduced by Medium Supplementation With L-Glutamine in Human Colorectal Caco-2 Cells," Int. J. Mol. Med. 22:825-832 (2008).
Finn et al., "Dasatinib, an Orally Active Small Molecule Inhibitor of Both the src and abl Kinases, Selectively Inhibits Growth of Basal-Type/'Triple-Negative' Breast Cancer Cell Lines Growing in Vitro," Breast Cancer Res. Treat. 105:319-26 (2007).
Fritz et al., "Rho GTPases are Over-Expressed in Human Tumors," Int. J. Cancer. 81:682-687 (1999).
Fuji, "Biochemical Studies of DBL-Transformation," Dissertation, Cornell University (Aug. 2005).
Gallagher et al., "13C MR Spectroscopy Measurements of Glutaminase Activity in Human Hepatocellular Carcinoma Cells Using Hyperpolarized 13C-Labeled Glutamine," Magn. Reson. Med. 60(2):253-257 (2008).
Gao et al., "c-Myc Suppression of miR-23 Enhances Mitochondrial Glutaminase and Glutamine Metabolism," Author Manuscript published in Nature 458(7239):762-765 (2009).
Georgopoulos et al., "Regulatory Sites and Effects of D-(3H)Aspartate Release From Rat Cerebral Cortex," Neurochem. Res. 20(1):45-49 (1995).
Ghosh et al., "Modulation of Tumor Induced Angiogenesis in Ehrlich Ascites Tumor," J. Exp. Clin. Cancer Res. 23(4):681-690 (2004).
Gladilina et al., "Cloning, Expression and Purification of Helicobacter pylori L-Asparaginase," Biomed. Khim. 54(4):482-486 (2008) (abstract only).
Gluck et al., "Implications for Altered Glutamate and GABA Metabolism in the Dorsolateral Prefrontal Cortex of Aged Schizophrenic Patients," Am. J. Psychiatry 159:1165-1173 (2002).
Gusak et al., "Synthesis of Fused Derivatives of 4,7-Phenanthroline by Condensation of 6-Aminoquinoline With Aromatic Aldehydes and Dimedone," Russian J. Org. Chem. 37(10):1495-1502 (2001) (abstract).
Hampson et al., "The PDZ Protein Tip-1 Is a Gain of Function Target of the HPV16 E6 Oncoprotein," Int. J. Oncol. 25(5):1249-1256 (2004).
Holten et al., "Glutamine as a Precursor for Transmitter Glutamate, Aspartate and GABA in the Cerebellum: A Role for Phosphate-Activated Glutaminase," J. Neurochem. 104(4):1032-1042 (2008).
Hunt et al., "Expression and Activity of pH-Regulatory Glutaminase in the Human Airway Epithelium," Am. J. Respir. Crit. Care Med. 165:101-107 (2002).
Joyce et al., "Integration of Rac-Dependent Regulation of Cyclin D1 Transcription Through a Nuclear Factor-κB-Dependent Pathway," J. Biol. Chem. 274:25245-25249 (1999).
Jung et al., "2,3,7,8-Tetrachlorodibenzo-p-dioxin (TCDD) Inhibits Neurite Outgrowth in Differentiating Human SH-SY5Y Neuroblastoma Cells," Toxicol. Lett. 188(2):153-156 (2009).
Kanamori et al., "The PDZ Protein Tax-Interacting Protein-1 Inhibits Beta-Catenin Transcriptional Activity and Growth of Colorectal Cancer Cells," J. Biol. Chem. 278(40):38758-38764 (2003).
Kaufmann et al., "Glutamine Affects Glutathione Recycling Enzymes in a DMBA-Induced Breast Cancer Model," Nutr. Cancer 60(4):518-525 (2008).
Kenny et al., "Bacterial Expression, Purification and Characterization of Rat Kidney-Type Mitochondrial Glutaminase," Protein Expr. Purif. 31:140-148 (2003).
Kita et al., "Down-Regulation of Glutaminase C in Human Hepatocarcinoma Cell by Diphenylarsinic Acid, a Degradation Product of Chemical Warfare Agents," Toxicol. Appl. Pharmacol. 220(3):262-270 (2007).
Kita et al., "Structure-Effect Relationship in the Down-Regulation of Glutaminase in Cultured Human Cells by Phenylarsenic Compounds," Toxicology 258(2-3):157-163 (2009).
Kobayashi & Millhorn, "Hypoxia Regulates Glutamate Metabolism and Membrane Transport in Rat PC12 Cells," J. Neurochem. 76:1935-1948 (2001).
Kvamme et al., "Evidence for Compartmentalization of Glutamate in Rat Brain Synaptosomes Using the Glutamate Sensitivity of Phosphate-Activated Glutaminase as a Functional Test," Neurosci. Lett. 25(2):193-198 (1981).
Kvamme et al., "Evidence Indicating That Pig Renal Phosphate-Activated Glutaminase Has a Functionally Predominant External Localization in the Inner Mitochondrial Membrane," J. Biol. Chem. 266(20):13185-13192 (1991).

(56) References Cited

OTHER PUBLICATIONS

Kvamme et al., Kinetics and Localization of Brain Phosphate Activated Glutaminase, *J. Neurosci. Res.* 66(5):951-958 (2001).
Kvamme et al., "Novel Form of Phosphate Activated Glutaminase in Cultured Astrocytes and Human Neuroblastoma Cells, PAG in Brain Pathology and Localization in the Mitochondria," *Neurochem. Res.* 33(7):1341-1345 (2008).
Kvamme et al., "Properties of Phosphate Activated Glutaminase in Astrocytes Cultured From Mouse Brain," *Neurochem. Res.* 7(6):761-770 (1982).
Lima et al., "Walker 256 Tumour Growth Causes Marked Changes of Glutamine Metabolism in Rat Small Intestine," *Cell Biochem. Funct.* 29(2):107-113 (2002).
Lin et al., "Specific Contributions of the Small GTPases Rho, Rac and Cdc42 to Dbl Transformation," *J. Biol. Chem.* 274:23633-23641 (1999).
Lora et al., "Antisense Glutaminase Inhibition Decreases Glutathione Antioxidant Capacity and Increases Apoptosis in Ehrlich Ascitic Tumour Cells," *Eur. J. Biochem.* 271:4298-4306 (2004).
Magedov et al., "Discovery and Investigation of Antiproliferative and Apoptosis-inducing Properties of New Heterocyclic Podophyllotoxin Analogues Accessible by a One-Step Multicomponent Synthesis," J. Med. Chem. 50:5186 (2007).
Maity et al., "Neovascularisation Offers a New Perspective to Glutamine Related Therapy," *Indian. J. Exp. Biol.* 38(1):88-90 (2000).
Martin-Rufian et al., "Identification of Genes Downregulated in Tumor Cells Expressing Antisense Glutaminase mRNA by Differential Display," *Cancer Biol. Therapy* 5(1):54-58 (2006).
Matés et al., "Glutamine Homeostasis and Mitochondrial Dynamics," *Int. J. Biochem. Cell Biol.* 41(10):2051-2061 (2009).
Mcgivan et al., "Glutaminase Isofom Expression in Cell Lines Derived from Human Colorectal Adenomas and Carcinomas," Biochem. J. 370:403 (2003).
Medina, "Glutamine Metabolism: Nutritional and Clinical Significance," *J. Nutr.* 131:2539S-2542S (2001).
Medina et al., "Relevance of Glutamine Metabolism to Tumor Cell Growth," *Mol. Cell. Biochem.* 113:1-15 (1992).
Nag, "Effect of Organophosphate Pesticides on Glutaminase and Glutamine Synthetase Activity in Rat Brain," *Indian J. Exp. Biol.* 30(6):543-545 (1992).
[No Authors Listed], "[The Regulatory Action of Dipeptide 'Deglutam' on the Glutamine Metabolized Enzymes in the Carcinosarcoma SM-1 Cells]," *Biomed. Khim.* 51(1):48-52 (2005) (abstract only).
Novak et al., "Androgen Secretion by Rcho-1 Cells Is Independent of Extracellular Glutamate Concentration," *Placenta* 25(6):548-552 (2004).
Ochiai et al., "Characterization of Several Amino Acid Transports and Glutamine Metabolish in MOLT4 Human T4 Leukemia Cells," *Clin. Lab Haematol.* 28(6):399-404 (2006).
Osbakken et al., "Effect of Cyclocreatine Feeding on Levels of Amino Acids in Rat Hearts Before and After an Ischemic Episode," *Am. J. Physiol. Heart Circ. Physiol.* 261(6):H1919-26 (1991).
PCT/US10/28688, International Search Report and Written Opinion (dated Sep. 23, 2010).
Perez-Gomez et al., "Co-Expression of Glutaminase K and L Isoenzymes in Human Tumour Cells," *Biochem. J.* 386(Pt. 3):535-542 (2005).
Perona et al., "Activation of the Nuclear Factor-κB by Rho, CDC42, and Rac-1 Proteins," *Genes Dev.* 11:463-475 (1997).
Pickering et al., "Pharmacological Inhibitors of NF-κB Accelerate Apoptosis in Chronic Lymphocytic Leukemia Cells," *Oncogene* 26:1166-1177 (2007).
Porter et al., "Complexity and Species Variation of the Kidney-type Glutaminase Gene," *Physiol. Genomics* 9:157-166 (2002).
Prakasham et al., "Evaluation of Antineoplastic Activity of Extracellular Asparaginase Produced by Isolated Bacillus Circulans," *Appl. Biochem. Biotechnol.* 160(1):72-80 (2010).

Preuss et al., "Effects of Glutamine Deamination on Glutamine Deamidation in Rat Kidney Slices," *J. Clin. Invest.* 52(4):755-764 (1973).
Reinert et al., "Role of Glutamine Depletion in Directing Tissue-Specific Nutrient Stress Responses to L-Asparaginase," *J. Biol. Chem.* 281(42):31222-31233 (2006).
Roberg et al., "Kinetics of a Novel Isoform of Phosphate Activated Glutaminase (PAG) in SH-SY5Y Neuroblastoma Cells," *Neurochem. Res.* 35(6):875-880 (2009).
Robinson et al., "Novel Mechanism of Inhibition of Rat Kidney-Type Glutaminase by Bis-2-(5-Phenylacetamido-1,2,4-Thiadiazol-2-yl)Ethly Sulfide (BPTES)," Biochem. J. 406:407-14 (2007).
Roy et al., "Acivicin With Glutaminase Regulates Proliferation and Invasion of Human MCF-7 and OAW-42 Cells—An in Vitro Study," *Indian J. Exp. Biol.* 46(1):22-26 (2008).
Roy et al., "Modulation of Metastatic Potential of B16F10 Melanoma Cells by Acivicin: Synergistic Action of Glutaminase and Potentiation of Cisplatin Cytotoxicity," *Asian Pac. J. Cancer Prev.* 8(2):301-036 (2007).
Segura et al., "Ehrlich Ascites Tumor Cells Expressing Anit-Sense Glutaminase mRNA Lose Their Capacity to Evade the Mouse Immune System," *Int. J. Cancer* 91:379-384 (2001).
Segura et al., "Inhibition of Glutaminase Expression Increases Sp1 Phosphorylation and Sp1/Sp3 Transcriptional Activity in Ehrlich Tumor Cells," *Cancer Lett.* 218(1):91-98 (2005).
Shimizu et al., "Bcl-2 Family Proteins Regulate the Release of Apoptogenic Cytochrome c by the Mitochondrial Channel VDAC," *Nature* 399:483-487 (1999).
Snodgrass et al., "Allosteric Properties of Phosphate-Activated Glutaminase of Human Liver Mitochondria," *Biochim. Biophys. Acta* 798(1):21-27 (1984).
Sovak et al., "Aberrant Nuclear Factor-kB/Rel Expression and the Pathogenesis of Breast Cancer," *J. Clin. Invest.* 100:2952-2960 (1997).
Svoboda et al., "Glutamine-Induced Apoptosis in Microglia Is Mediated by Mitochondrial Dysfunction," *Eur. J. Neurosci.* 30(2):196-206 (2009).
Szeliga et al., "Glutamine in Neoplastic Cells: Focus on the Expression and Roles of Glutaminases," *Neurochem. Int.* 55(1-3):71-75 (2009).
Szeliga et al., "Lack of Expression of the Liver-Type Glutaminase (LGA) mRNA in Human Malignant Gliomas," *Neurosci. Lett.* 374(3):171-173 (2005).
Szeliga et al., "Relative Expression of mRNAS Coding for Glutaminase Isoforms in CNS Tissues and CNS Tumors," *Neurochem. Res.* 33(5):808-813 (2008).
Szeliga et al., "Transfection With Liver-Type Glutaminase cDNA Alters Gene Expression and Reduces Survival, Migration and Proliferation of T98G Glioma Cells," *Glia.* 57(9):1014-1023 (2009).
Taylor et al., "A Phase I and Pharmacodynamic Evaluation of Polyethylene Glycol-Conjugated L-Asparaginase in Patients with Advanced Solid Tumors," *Cancer Chemother. Pharmacol.* 47:83-88 (2001).
Timms et al., "Evaluation of Two-Dimensional Differential Gel Electrophoresis for Proteomic Expression Analysis of a Model Breast Cancer Cell System," *Mol. Cell. Proteomics* 1:96 (2002).
Turner et al "Glutaminase Isoform Expression in Cell Lines Derived from Human Colorectal Adenomas and Carcinomas," *Biochem. J.* 370:403-408 (2003).
Valastyan et al., "A Pleiotropically Acting microRNA, miR-31, Inhibits Breast Cancer Metastasis," *Cell* 137:1032-1046 (2009).
Wheeler & Ridley, Review, "Why Three Rho Proteins? RhoA, RhoB, RhoC, and Cell Motility," Experimental Cell Res. 301:43-49 (2004).
Whitehead et al., "Dependence of Dbl and Dbs Transformation on MEK and NF-kappaB Activation," *Mol. Cell Biol.* 19:7759-7770 (1999).
Wiessner et al., "Localization and Possible Function of the Glutamate Transporter, EAAC1, in the Rat Retina," *Cell Tissue Res.* 310(1):31-40 (2002).
Wojcik et al., "Glutamine-Dependent NAD+ Synthetase. How a Two-Domain, Three-Substrate Enzyme Avoids Waste," *J. Biol. Chem.* 281(44):33395-33402 (2006).

(56) References Cited

OTHER PUBLICATIONS

Yamaoka T., "[GMP Synthetase]," *Nihon Rinsho* 61(Suppl 1):66-70 (2003).

Ye et al., "(1R,3S)-1-Aminocyclopentane-1,3-Dicarboxylic Acid (RS-ACPD) Reduces Intracellular Glutamate Levels in Astrocytes," *J Neurochemistry* 79(4):756-766 (2001).

Zacharias et al., "Human Cutaneous Melanoma Expresses a Significant Phosphate-Dependent Glutaminase Activity: A Comparison With the Surrounding Skin of the Same Patient," *Cell Biochem. Funct.* 21(1):81-84 (2003).

Zielke et al., "Functional Intracellular Glutaminase Activity in Intact Astrocytes," *Neurochem. Res.* 14(4):327-332 (1989).

\* cited by examiner

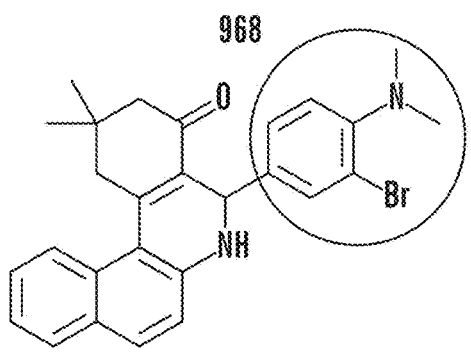
968
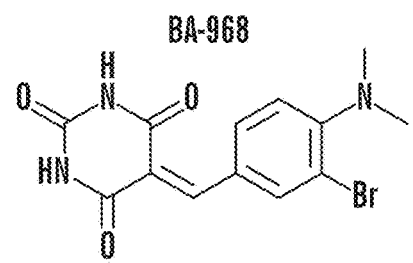
BA-968
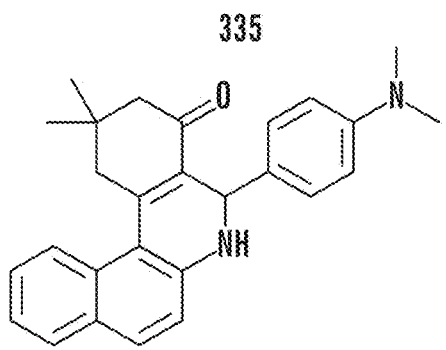
335
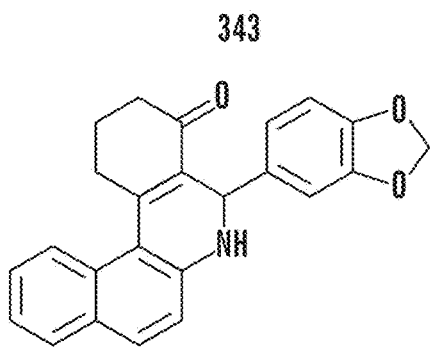
343
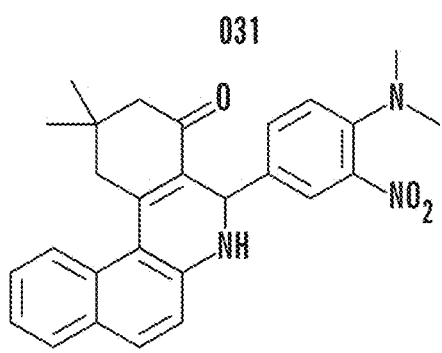
031
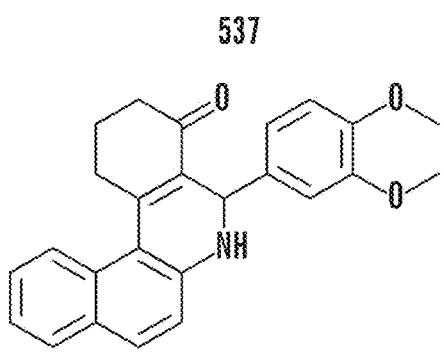
537
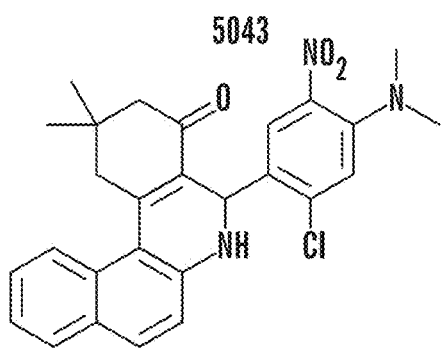
5043
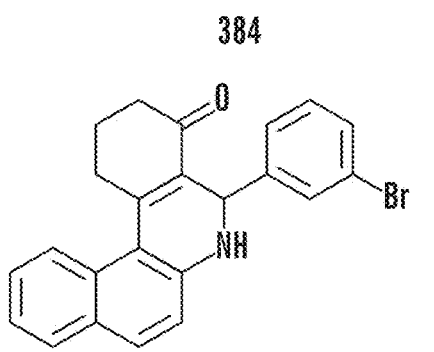
384
*FIG. 1C*

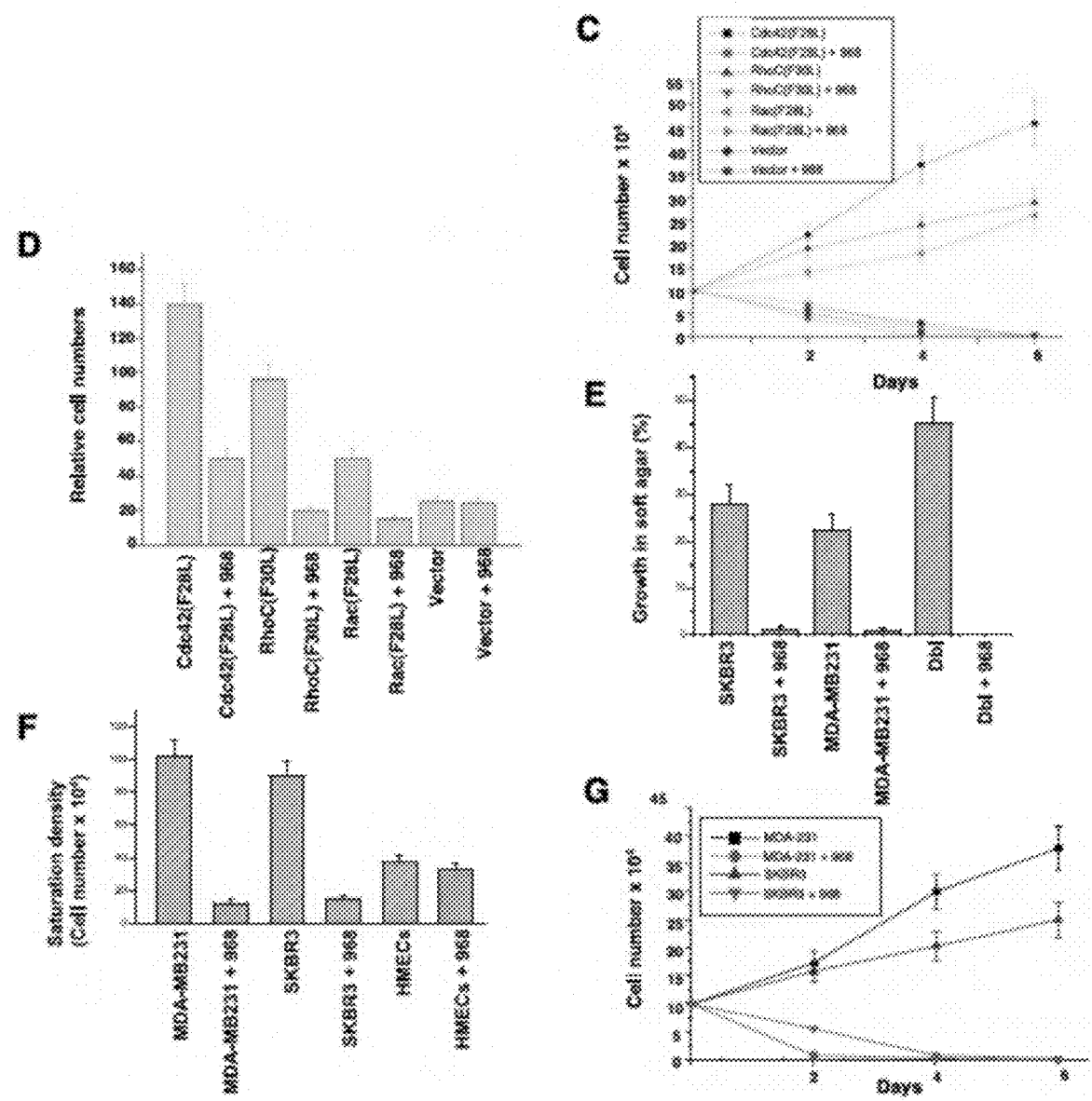
FIGS. 2C-G

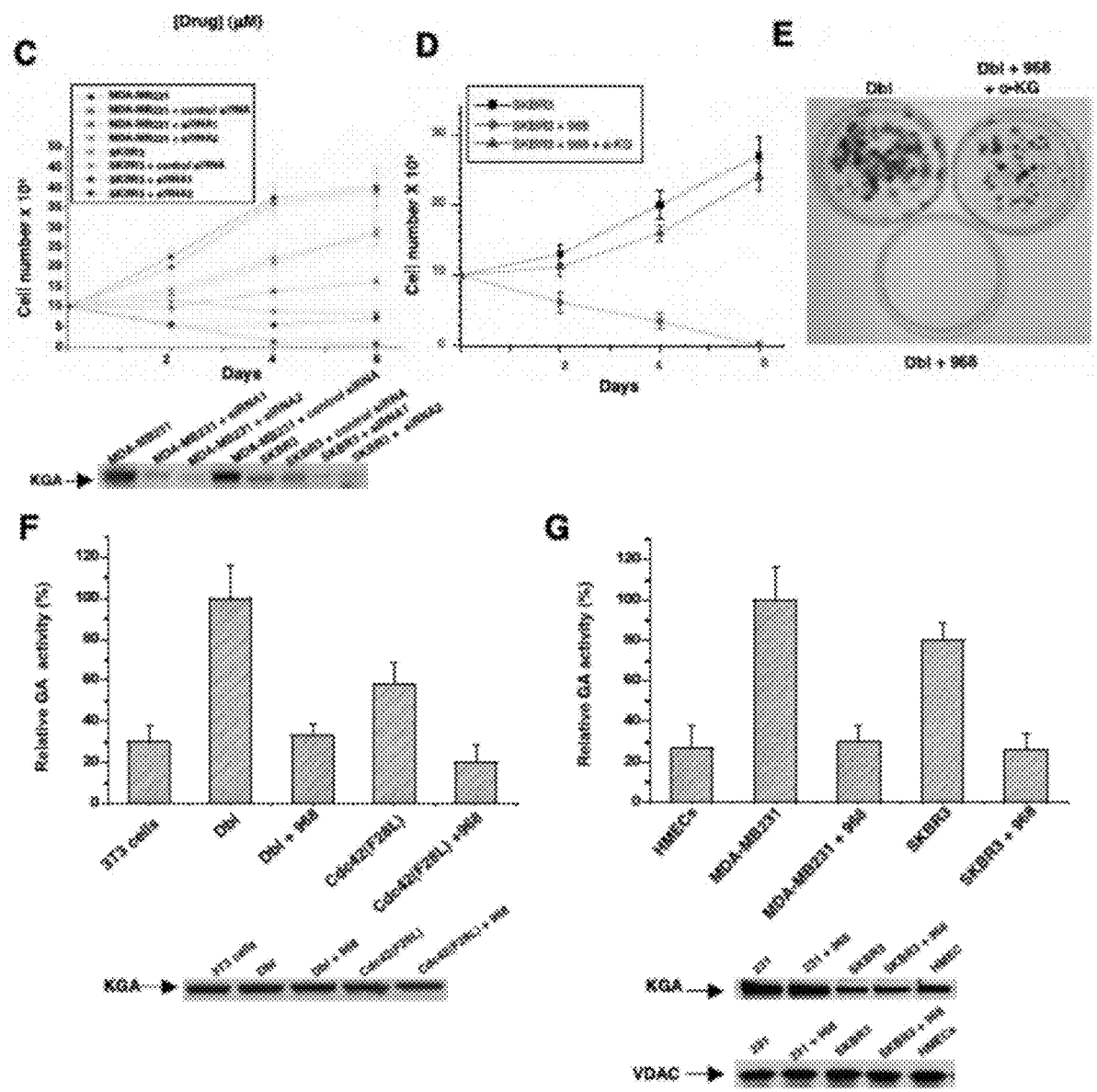
FIGS. 3C-G

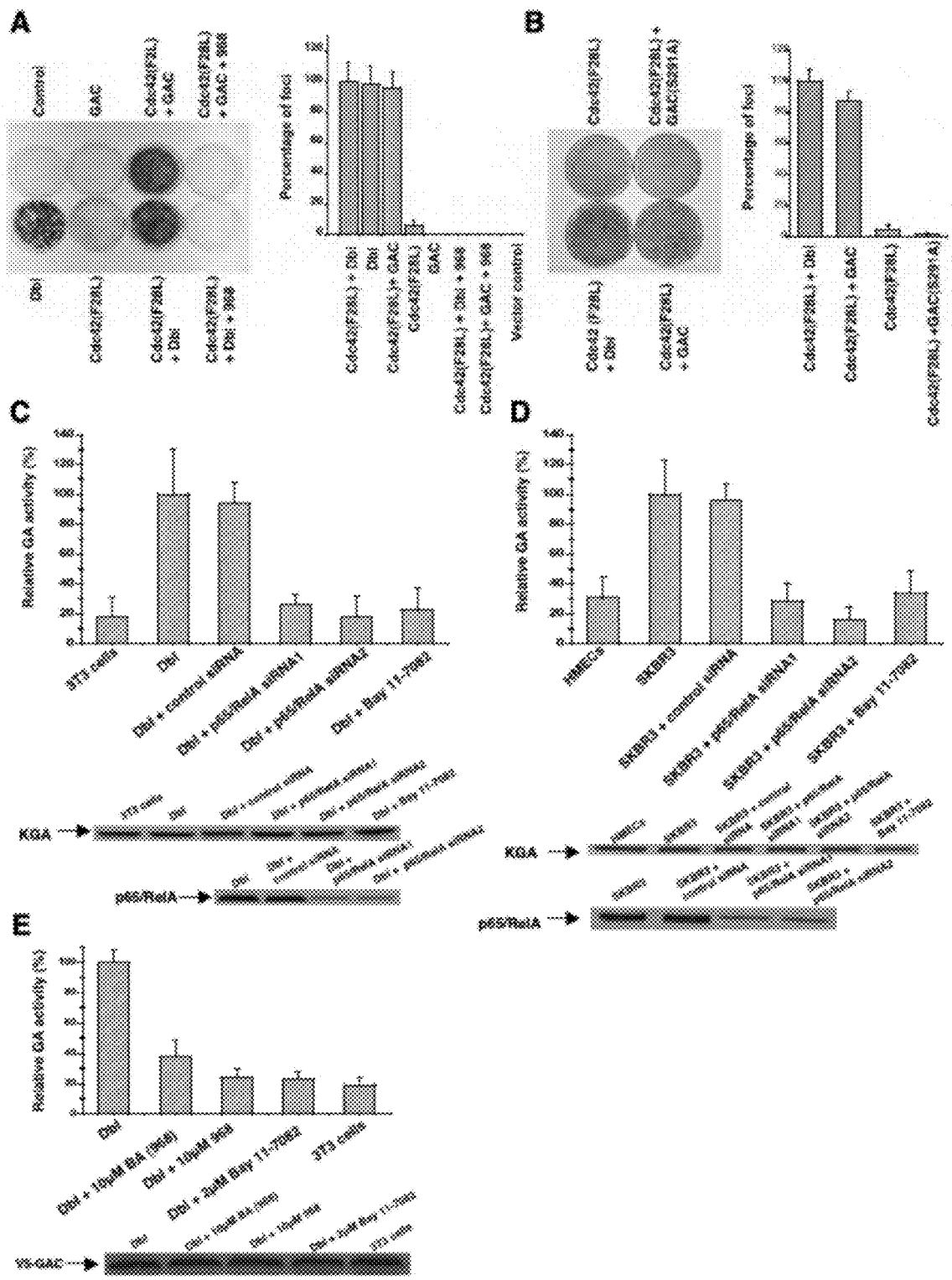
FIGS. 4A-E

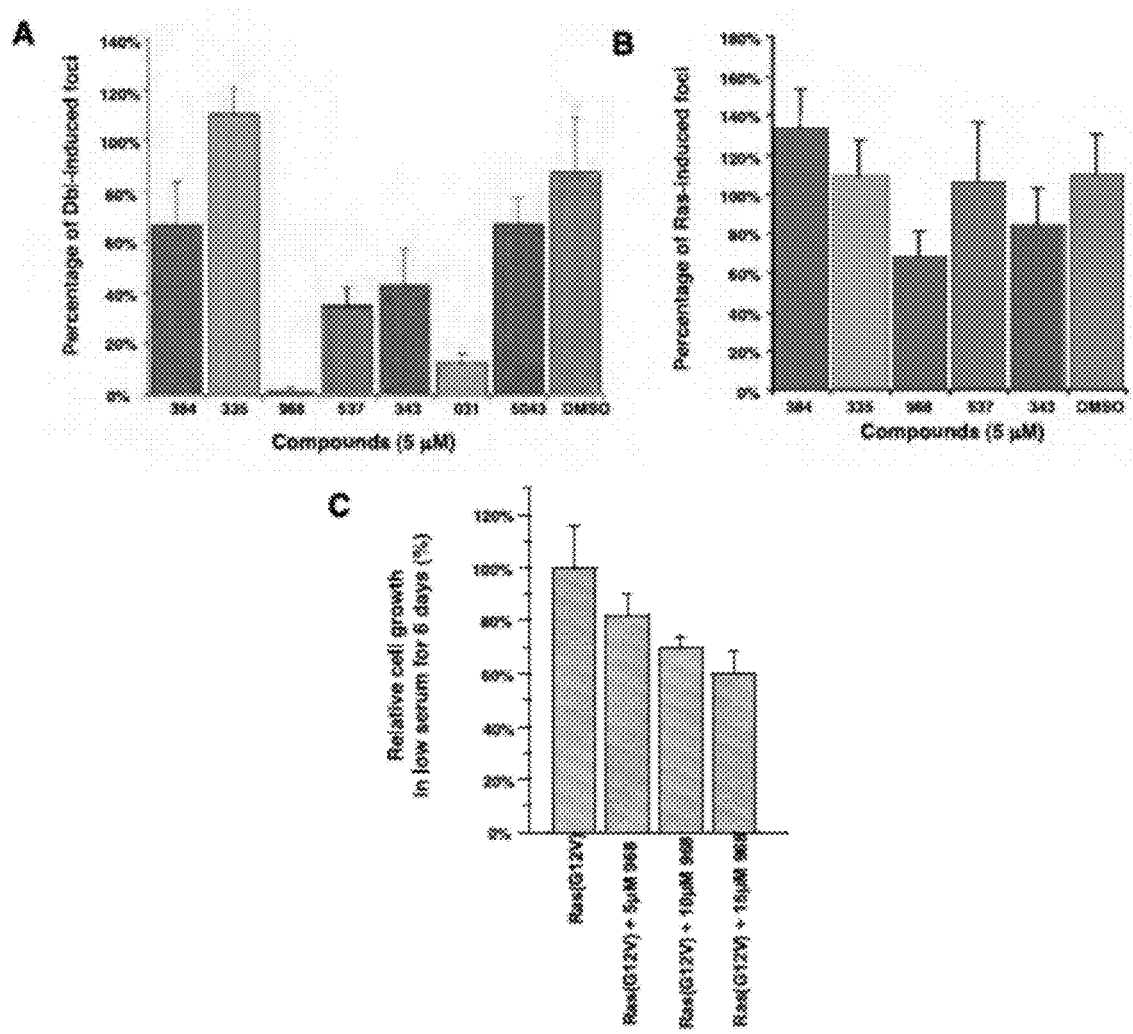
FIGS. 5A-C

SEQUENCE LISTING

```
<160> NUMBER OF SEQ ID NOS: 4

<210> SEQ ID NO 1
<211> LENGTH: 674
<212> TYPE: PRT
<213> ORGANISM: Mus musculus

<400> SEQUENCE: 1

Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
            20                  25                  30

Thr Leu Cys Arg Arg Pro Arg Gly Gly Ser Arg Pro Thr Ala Gly Leu
        35                  40                  45

Val Ala Ala Ala Arg Leu His Pro Trp Trp Gly Gly Gly Arg Ala
    50                  55                  60

Lys Gly Pro Gly Ala Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
        115                 120                 125

Val Ala Ala Gly Asp Asn Lys Ile Lys Gln Gly Leu Leu Pro Ser Leu
    130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
```

```
                      325                 330                 335
Pro Met Val Asn Ala Gly Ala Ile Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
        370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
                420                 425                 430

Ser Val Met Ala Ala Thr Leu Ala Asn Gly Gly Phe Cys Pro Ile Thr
            435                 440                 445

Gly Glu Arg Val Leu Ser Pro Glu Ala Val Arg Asn Thr Leu Ser Leu
        450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Ile Leu Leu Val
                485                 490                 495

Val Pro Asn Val Met Gly Met Met Cys Trp Ser Pro Leu Asp Lys
            500                 505                 510

Met Gly Asn Ser Val Lys Gly Ile His Phe Cys His Asp Leu Val Ser
        515                 520                 525

Leu Cys Asn Phe His Asn Tyr Asp Asn Leu Arg His Phe Ala Lys Lys
        530                 535                 540

Leu Asp Pro Arg Arg Glu Gly Gly Asp Gln Arg Val Lys Ser Val Ile
545                 550                 555                 560

Asn Leu Leu Phe Ala Ala Tyr Thr Gly Asp Val Ser Ala Leu Arg Arg
                565                 570                 575

Phe Ala Leu Ser Ala Met Asp Met Glu Gln Arg Asp Tyr Asp Ser Arg
            580                 585                 590

Thr Ala Leu His Val Ala Ala Ala Glu Gly His Val Glu Val Val Lys
        595                 600                 605

Phe Leu Leu Glu Ala Cys Lys Val Asn Pro Phe Pro Lys Asp Arg Trp
    610                 615                 620

Asn Asn Thr Pro Met Asp Glu Ala Leu His Phe Gly His His Asp Val
625                 630                 635                 640

Phe Lys Ile Leu Gln Glu Tyr Gln Val Gln Tyr Thr Pro Gln Gly Asp
                645                 650                 655

Ser Asp Asp Gly Lys Gly Asn Gln Thr Val His Lys Asn Leu Asp Gly
            660                 665                 670

Leu Leu

<210> SEQ ID NO 2
<211> LENGTH: 603
<212> TYPE: PRT
<213> ORGANISM: Mus musculus

<400> SEQUENCE: 2

Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
```

```
                     20                  25                  30
Thr Leu Cys Arg Arg Pro Arg Gly Gly Ser Arg Pro Thr Ala Gly Leu
                 35                  40                  45

Val Ala Ala Ala Arg Leu His Pro Trp Trp Gly Gly Gly Arg Ala
 50                  55                  60

Lys Gly Pro Gly Ala Gly Gly Leu Ser Ser Pro Ser Glu Ile Leu
 65                  70                  75                  80

Gln Glu Leu Gly Lys Gly Gly Thr Pro Pro Gln Gln Gln Gln Gln
                 85                  90                  95

Gln Gln Gln Pro Gly Ala Ser Pro Pro Ala Ala Pro Gly Pro Lys Asp
                100                 105                 110

Ser Pro Gly Glu Thr Asp Ala Phe Gly Asn Ser Glu Gly Lys Glu Met
                115                 120                 125

Val Ala Ala Gly Asp Asn Lys Ile Lys Gln Gly Leu Leu Pro Ser Leu
                130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
                180                 185                 190

Thr Thr Ser Asp Gly Val Met Leu Asp Lys Asp Leu Phe Lys Lys Cys
                195                 200                 205

Val Gln Ser Asn Ile Val Leu Leu Thr Gln Ala Phe Arg Arg Lys Phe
                210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
                260                 265                 270

Val Asp Gly Gln Arg His Ser Ile Gly Asp Thr Lys Val Pro Phe Cys
                275                 280                 285

Leu Gln Ser Cys Val Lys Pro Leu Lys Tyr Ala Ile Ala Val Asn Asp
                290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
                340                 345                 350

Gly Val Asn Asn Ala Glu Lys Phe Asp Tyr Val Met Gln Phe Leu Asn
                355                 360                 365

Lys Met Ala Gly Asn Glu Tyr Val Gly Phe Ser Asn Ala Thr Phe Gln
                370                 375                 380
```

```
Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
            405                 410                 415

Asp Phe Tyr Phe Gln Leu Cys Ser Ile Glu Val Thr Cys Glu Ser Ala
        420                 425                 430

Ser Val Met Ala Ala Thr Leu Ala Asn Gly Gly Phe Cys Pro Ile Thr
    435                 440                 445

Gly Glu Arg Val Leu Ser Pro Glu Ala Val Arg Asn Thr Leu Ser Leu
450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Ile Leu Leu Val
            485                 490                 495

Val Pro Asn Val Met Gly Met Cys Trp Ser Pro Leu Asp Lys
                500                 505                 510

Met Gly Asn Ser Val Lys Gly Ile His Phe Cys His Asp Leu Val Ser
            515                 520                 525

Leu Cys Asn Phe His Asn Tyr Asp Asn Leu Arg His Phe Ala Lys Lys
            530                 535                 540

Leu Asp Pro Arg Arg Glu Gly Gly Asp Gln Arg His Ser Phe Gly Pro
545                 550                 555                 560

Leu Asp Tyr Glu Ser Leu Gln Gln Glu Leu Ala Leu Lys Asp Thr Val
                565                 570                 575

Trp Lys Lys Val Ser Pro Glu Ser Ser Asp Asp Thr Ser Thr Thr Val
            580                 585                 590

Val Tyr Arg Met Glu Ser Leu Gly Glu Arg Ser
            595                 600

<210> SEQ ID NO 3
<211> LENGTH: 8
<212> TYPE: PRT
<213> ORGANISM: Mus musculus

<400> SEQUENCE: 3

Val Leu Ser Pro Glu Ala Val Arg
1               5

<210> SEQ ID NO 4
<211> LENGTH: 16
<212> TYPE: PRT
<213> ORGANISM: Mus musculus

<400> SEQUENCE: 4

Val Ser Pro Glu Ser Ser Asp Asp Thr Ser Thr Thr Val Val Tyr Arg
1               5                   10                  15
```

INHIBITION OF GLUTAMINASE C

This application is a divisional of U.S. patent application Ser. No. 13/259,533, which is a national stage application under 35 U.S.C. § 371 of International Patent Application No. PCT/US10/28688, filed Mar. 25, 2010, which claims the benefit of U.S. Provisional Patent Application Ser. No. 61/163,304, filed Mar. 25, 2009, which is hereby incorporated by reference in its entirety.

This invention was made with government support under grant numbers RO1 GM40654, RO1 GM47458, and RO1 GM61762 awarded by National Institutes of Health. The government has certain rights in the invention.

FIELD OF INVENTION

The present invention relates to the inhibition of glutaminase C (GAC).

BACKGROUND OF THE INVENTION

Tumor cells have an absolute requirement for glutamine as a growth substrate. Glutamine is required as a precursor for both DNA synthesis and protein synthesis, and may also be used as a respiratory substrate. In experiments where glutamine metabolism in tumor cells has been specifically compared with that in non-transformed cells of the same origin, glutamine metabolism in the tumor cells has been found to be considerably faster. This is true for human hepatocytes and hepatoma cells (Souba, W., "Glutamine and Cancer," *Ann. Surg.* 218:715-728 (1993)) and also for glutamine oxidation in rat kidney fibroblasts and rat fibrosarcoma cells (Fischer et al., "Adaptive Alterations in Cellular Metabolism and Malignant Transformation," *Ann. Surg.* 227:627-634 (1998)).

The first reaction in glutamine metabolism is hydrolysis of glutamine to glutamate via the mitochondrial enzyme phosphate-dependent glutaminase. Two major isoforms of this enzyme have been characterized. These are known as the kidney form (K-type) which was first cloned from rat kidney (Shapiro et al., "Isolation, Characterisation, and In vitro Expression of a cDNA That Encodes the Kidney Isoenzyme of the Mitochondrial Glutaminase," *J. Biol. Chem.* 266:18792-18796 (1991)) and is expressed in many mammalian tissues, and the liver form (L-type) (Chung-Bok et al., "Rat Hepatic Glutaminase, Identification of the Full Coding Sequence and Characterisation of a Functional Promoter," *Biochemn. J.* 324:193-200 (1997)) which was originally identified in post-natal liver. These two enzymes have different kinetic properties. Although the cDNAs encoding the two isoforms have regions of high sequence similarity, they also differ significantly elsewhere and the enzyme isoforms are the products of different genes (for a review see (Curthoys et al., "Regulation of Glutaminase Activity and Glutamine Metabolism," *Annu. Rev. Nutr.* 16:133-159 (1995)). Glutamine metabolism is essential for tumor cell growth but there are few studies at present on glutaminase expression in tumor cells. In mouse Ehrlich ascites cells (Quesada et al., "Purification of Phosphate-Dependent Glutaminase from Isolated Mitochondria of Ehrlich Ascites-Tumor Cells," *Biochem. J.* 255:1031-1035 (1988)) and rat fibrosarcoma cells (Fischer et al., "Adaptive Alterations in Cellular Metabolism and Malignant Transformation," *Ann. Surg.* 227:627-634 (1998)), an enzyme with the kinetic properties of the K-type glutaminase is expressed. Rat and human hepatocytes express the L-type glutaminase, but this is not expressed in hepatoma cell lines, which express the K-type instead (Souba, W. W., "Glutamine and Cancer," *Ann. Surg.* 218:715-728 (1993)). Inhibition of K-type glutaminase expression by anti-sense mRNA in Ehrlich ascites cells has been shown to decrease the growth and tumorigenicity of these cells (Lobo et al., "Inhibition of Glutaminase Expression by Antisense mRNA Decreases Growth and Tumorigenicity of Tumor Cells," *Biochem. J.* 348:257-261 (2000)).

The present invention is directed to overcoming these and other deficiencies in the art.

SUMMARY OF THE INVENTION

A first aspect of the present invention relates to a method of reducing the production of glutamate from glutamine by glutaminase C in a cell or a tissue. The method involves inhibiting glutaminase C activity in the cell or tissue under conditions effective to reduce production of glutamate from glutamine.

A second aspect of the present invention relates to a method of treating a subject with a condition mediated by production of glutamate from glutamine by glutaminase C. The method involves selecting a subject with a condition mediated by production of glutamate from glutamine and administering to said selected subject an inhibitor of glutaminase C activity under conditions effective to treat the condition mediated by production of glutamate from glutamine.

A third aspect of the present invention relates to a pharmaceutical composition comprising a compound selected from the group consisting of:

(i) a compound of formula (II):

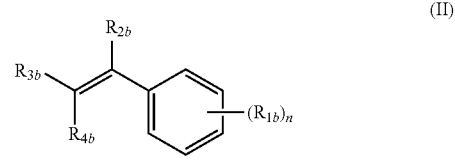

wherein:

n is an integer from 1 to 4;

$R_{1b}$ is independently at each occurrence H, OH, $OR_{5b}$, halogen, CN, $NO_2$, $NH_2$, $NHR_{5b}$, $NR_{5b}R_{6b}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen;

$R_{2b}$ is independently H, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or mono or polycyclic aryl;

$R_{3b}$ and $R_{4b}$ are independently H, $OR_{5b}$, $SR_{5b}$, $R_{5b}S(O)$—, $R_{5b}S(O)_2$—, —$COOR_{5b}$, —$C(O)NR_{5b}R_{6b}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen; or $R_{3b}$ and $R_{4b}$ can combine together to form a mono or polycyclic heterocyclyl or heteroaryl containing from 1-5 heteroatoms selected from the group consisting of nitrogen, sulfur, and oxygen, each formed heteroaryl or heterocyclyl optionally substituted with substituents selected from the group consisting of oxo, thio, amino, $C_1$-$C_6$ alkyl, $C_2$-$C_6$ alkenyl, and $C_2$-$C_6$ alkynyl; and $R_{5b}$ and $R_{6b}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen, each one of $R_{5b}$ or $R_{6b}$, optionally substituted from 1 to 3 times with substituents selected from the group consisting of H, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl;

(ii) a compound of formula (III):

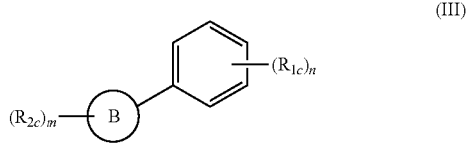

(III)

wherein:

m and n are integers from 1 to 4;

B is a substituted or unsubstituted mono or polycyclic aryl or mono or polycyclic heterocyclyl or heteroaryl with each cyclic unit containing from 1 to 5 heteroatoms selected from the group consisting of nitrogen, sulfur, and oxygen;

$R_{1c}$ and $R_{2c}$ are independently H, OH, $OR_{3c}$, halogen, CN, $NO_2$, COOH, $NH_2$, $NHR_k$, $NR_{3c}R_{4c}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen; and $R_{3c}$ and $R_{4c}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen; and (iii) a compound comprising the active moiety of formula II or formula III.

A fourth aspect of the present invention relates to the compound of formula:

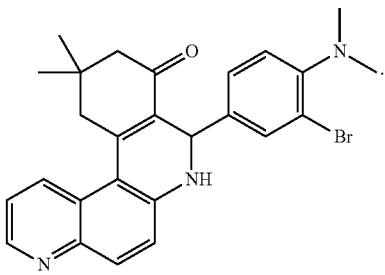 [SMILES: CN(C)c1ccc(C2Nc3ccc4ncccc4c3C3=C2C(=O)CC(C)(C)C3)cc1Br]

A fifth aspect of the present invention relates to the method of screening for compounds capable of reducing the production of glutamate from glutamine. The method involves providing a cell or tissue under conditions effective for the cell or tissue to produce glutamate from glutamine as a result of glutaminase C activity. A plurality of candidate compounds is then provided to contact the cell or tissue and the candidate compounds which inhibit glutaminase C activity as a result of said contacting are identified.

It has been found that V5-tagged GAC, when ectopically expressed in Dbl-transformed cells followed by its immunoprecipitation (IP), exhibit significantly higher activity compared to V5-GAC IPed from non-transformed NIH 3T3 cells. The GA activity IPed from Dbl-transformed cells is inhibited by the methods as well as the compounds of the present invention, and is markedly reduced when NF-kB activation is blocked prior to IP. This is consistent with the suggestion that GAC is modified in transformed cells in an NF-kB-dependent manner.

Also described is the importance of cellular metabolism in the development of cancer and, in particular, the early observations that tumor cells exhibit enhanced glycolytic activity (i.e. the "Warburg effect"). In particular, a novel regulatory connection between the Rho GTPases and the activation of the mitochondrial enzyme glutaminase C is described, thus shedding new light on how glutamine metabolism is elevated in tumorigenesis. These findings raise interesting possibilities regarding the targeting of the enzyme activity of glutaminase C as a potential therapeutic strategy against malignant transformation.

In addition, the present invention offers an entirely novel approach to identification and development of drugs designed to inhibit the function of glutaminase C. Since it is well-known that tumorigenesis is linked to glutamine metabolism, the present invention can have an important impact in anti-cancer drug development.

BRIEF DESCRIPTION OF THE DRAWINGS

FIGS. 1A-E illustrate that the small molecule 968 inhibiting cellular transformation. FIG. 1A shows NIH 3T3 cells that are transiently transfected with oncogenic Dbl and cultured for 14 days, while treated with different benzo[a]phenanthridinones (designated 384, 335, 968, 537, and 343) (10 μM each). Cells were fixed and stained with crystal violet for counting of foci. Right: 968 was serially diluted (10, 5, 2.5, and 1.25 μM) and evaluated for its ability to inhibit focus formation. FIG. 1B shows NIH 3T3 cells that are stably transfected with Dbl and grown in DMEM supplemented with 1% calf serum and the indicated amounts of 968 or BA-968. After 6 days, the cells are counted. 100% represents the number of Dbl-transformed cells counted in the absence of 968 ($27.5 \times 10^4$ cells). Data represent the average of 3 experiments (±s.d.). FIG. 1C shows the different benzo[a]phenanthridinone derivatives examined for their effects on Dbl-induced focus formation (designated 968, BA968, 335, 343, 031, 537, 5043, and 384). FIG. 1D shows control NIH 3T3 cells that are cultured in DMEM supplemented with 10% calf serum, and either untreated or treated with 10 μM 968 or 335. At the indicated times, the cells are counted. Data represent the average of 3 experiments (±s.d.). FIG. 1E shows photomicrographs of Dbl-transfected NIH 3T3 cells (bottom panels) and control NIH 3T3 cells (top panels) treated with either DMSO or 5 μM 968.

FIGS. 2A-G illustrate effects of 968 on the transforming activity of constitutively active Rho GTPases and human breast cancer cells. FIG. 2A (top) shows that NIH 3T3 cells stably expressing hemagglutinin (HA)-tagged Cdc42 (F28L), Rac(F28L), RhoC(F30L), or vector control cells, either treated with 10 μM 968 or untreated, are grown in soft agar. Cells are scored after 14 days and plotted as the percentage of the total number of colonies greater than 50 mm in diameter. Data represent the average of 3 experiments (±s.d.). FIG. 2A (bottom) shows the relative expression of the HA-tagged GTPases. FIG. 2B shows cells that are treated with 10 μM 968 or untreated, cultured in DMEM supplemented with 10% calf serum for 6 days, and then counted. Data represent the average of 3 experiments (±s.d.). FIG. 2C shows cells that are cultured in DMEM supplemented with 1% calf serum, treated with 10 μM 968 or untreated, and counted at the indicated times. Data represent the average of 3 experiments (±s.d.). FIG. 2D shows cells that are serum-starved, treated with 10 μM 968 or untreated, and seeded in MilliCell upper chambers containing growth factor-reduced Matri-gel. After 24 hours at 37° C. the migratory cells are fixed, stained with GIEMSA, and counted. Data represent the average of 3 experiments (±s.d.). FIG. 2E shows MDA-MB231 cells, SKBR3 cells, and NIH 3T3 cells stably expressing Dbl that are treated with 10 μM 968 or untreated, and grown in soft-agar as in FIG. 2A. Data represent the average of 3 experiments (±s.d.). FIG. 2F shows breast cancer cells that are cultured in RPMI 1640 medium supplemented with 10% fetal bovine serum, and HMECs are cultured in MEGM complete medium, for 6 days in the presence or absence of 10 μM 968, and then counted. Data represent the average of 3 experiments (±s.d.). FIG. 2G shows breast cancer cells that are cultured in RPMI 1640 medium supplemented with 1% fetal bovine serum, treated with 10 μM 968 or untreated, and analyzed as in 2C. Data represent the average of 3 experiments (±s.d.).

FIGS. 3A-G show that glutaminase C serves as a target for 968. FIG. 3A shows the *E. coli*-expressed mouse ortholog of human GAC that is assayed in the presence or absence of the indicated amounts of 968 (●) or 335 ( ). 100%=620 moles of glutamine hydrolyzed per minute per mole of enzyme. Data represent the average of 3 experiments (±s.d.). FIG. 3A (top panel) shows the biotin-labeled, active moiety of 968 linked to streptavidin-agarose beads, or control beads alone that is incubated with NIH 3T3 cell lysates transiently expressing V5-tagged mouse GAC. Following precipitation of the beads and re-suspension, the samples are analyzed by Western blotting with anti-V5 antibody. FIG. 3B (left) shows NIH 3T3 cells stably expressing HA-Cdc42(F28L), cells stably expressing HA-Cdc42(F28L) transfected with control siRNA or siRNAs targeting both isoforms of mouse KGA, or control cells that are grown in DMEM supplemented with 1% calf serum and counted. Data represent the average of 3 experiments (±s.d.). FIG. 3B (right) shows the efficiencies of siRNAs targeting both isoforms of KGA, and the relative levels of HA-Cdc42 in the different cells. FIG. 3C (top) shows breast cancer cells that are grown in RPMI 1640 medium supplemented with 1% fetal bovine calf serum. Data represent the average of 3 experiments (±s.d.). FIG. 3C (bottom) shows the relative efficiencies of siRNAs targeting both isoforms of KGA. FIG. 3D shows SKBR3 cells that are grown in 1% fetal bovine serum as in 3C except in the presence of 10 μM 968 alone or together with 7 μM dimethy α-ketoglutarate. Data represent the average of 3 experiments (±s.d.). FIG. 3E NIH 3T3 cells transiently expressing Dbl are assayed for focus formation in the presence of 10 μM 968 alone or together with 7 μM dimethyl α-ketoglutarate. FIG. 3F (top) shows mitochondrial fractions from equivalent numbers of the indicated stable cell lines, treated or untreated with 10 μM 968 that are assayed for basal (phosphate-independent) GA activity. 100%=680 nM glutamine hydrolyzed per minute per $10^5$ cells. Data are the average of 3 experiments (=s.d.). FIG. 3G (bottom) shows the relative amounts of KGA (using an antibody which recognizes both isoforms) in the mitochondrial preparations. FIG. 3G (top) shows the mitochondrial fractions from equivalent numbers of the indicated cells, treated or untreated with 10 μM 968, were assayed for basal (phosphate-independent) GA activity. 100%=750 nM glutamine hydrolyzed per minute per $10^5$ cells. Data represent the average of 3 experiments (±s.d.). FIG. 3G (bottom) shows the relative amounts of KGA and VDAC present in the mitochondrial preparations.

FIGS. 4A-E illustrate the role of glutaminase C activity in cellular transformation. FIG. 4A (left) shows control NIH 3T3 cells, NIH 3T3 cells transiently expressing Dbl, cells stably expressing Cdc42(F28L) and transiently expressing mouse GAC, cells stably expressing Cdc42(F28L), cells transiently expressing GAC alone, and cells stably expressing Cdc42(F28L) and transiently expressing Dbl that are examined for focus-forming activity. FIG. 4A (right) shows the quantification of foci. Data represent the average of 3 experiments (±s.d.). FIG. 4B (left) shows the focus-forming assays performed on NIH 3T3 cells stably expressing Cdc42 (F28L), cells stably expressing Cdc42(F28L) and transiently expressing Dbl, and cells stably expressing Cdc42(F28L) and either transiently expressing wild-type mouse GAC or the GAC(S291A) mutant. FIG. 4B (right) shows the quantification of foci. Data represent the average of 3 experiments (±s.d.). FIG. 4C (top) shows the basal (phosphate-independent) GA activity in the mitochondrial fractions from NIH 3T3 cells stably expressing Dbl that were cultured for 2 days and treated or untreated with 2 μM BAY 11-7082, or transfected with control siRNA or siRNAs targeting the p65/RelA subunit. 100% represents the activity measured in untreated Dbl-transformed cells. The data represent the average of 2 experiments. FIG. 4C (bottom) shows the relative amounts of KGA (using an antibody which recognizes both isoforms) present in the mitochondria from the indicated cells, and the relative efficiencies of two siRNAs targeting p65/RelA. FIG. 4D (top) shows the basal (phosphate-independent) GA activity in the mitochondrial fractions from HMECs, and SKBR3 cells treated or untreated with 2 μM BAY 11-7082, or transfected with siRNAs targeting p65/RelA. 100% represents the activity measured in untreated SKBR3 cells. The data represent the average of 2 experiments. FIG. 4D (bottom) shows the relative amounts of KGA (using an antibody which recognizes both isoforms) present in the mitochondria from the indicated cells, and the relative efficiencies of two siRNAs targeting p65/RelA. FIG. 4E (top) shows that V5-GAC was transiently expressed in NIH 3T3 cells stably expressing Dbl that were treated with 2 μM BAY 11-7082 or untreated, or in control NIH 3T3 cells, and then immunoprecipitated and assayed for GA activity in the absence of phosphate, and in the presence or absence of 10 μM 968 or BA-986. Data represent the average of 3 experiments (±s.d.). FIG. 4E (bottom) shows the relative expression of V5-GAC.

FIGS. 5A-C illustrate comparative abilities of 968 and other benzo[a]phenanthrldinones to inhibit the transforming activity of oncogenic Dbl and H-Ras. FIG. 5A shows NTH 313 cells that are transiently transfected with oncogenic Dbl for 14 days while treated with different benzo[a]phenanthridinones (designated 384, 335, 968, 537, 343, 031, and 5043, see FIG. 1C for structures) (5 μM, each) that are dissolved in DMSO. Histograms show the relative levels of Dbl-induced focus formation for the different treatments, compared to Dbl-induced focus formation measured in the presence of DMSO (i.e. solvent control). Data represent the average of 3 experiments (mean±s.d.). FIG. 5B shows NIH 3T3 cells that are transiently transfected with H-Ras(G12V) and cultured for 14 days, while treated with different benzo [a}phenanthridinones (5 μM, each) that are dissolved in DMSO. Histograms show the relative levels of Ras(G12V)-induced focus formation measured for the different treatments, compared to Ras(G12V)-induced focus formation measured in the presence of DMSO (solvent control). Data represent the average of 3 experiments (mean±s.d.). FIG. 5C NIH 3T3 cells stably expressing H-Ras(G12V) that are cultured in DMEM supplemented with 1% calf serum, with the indicated amounts of 968. After 6 days, cells are trypsinized and counted. 100% represents the number of cells counted in the absence of 968, i.e. 26×10$^4$ cells. Data represent the average of 3 experiments (mean±s.d.).

FIG. 7 illustrates the MS peptide analysis of the silver-stained band that was specifically precipitated by the biotin-labeled, active moiety of 968. Shown in the figure is the alignment of mouse kidney-type glutaminase (KGA) isoform-1 (SEQ ID NO: 1) and isoform-2 (the mouse ortholog of human GAC) (SEQ ID NO: 2). The peptides identified by the Maldi-MS analysis of the protein precipitated by the biotin-labeled, active moiety of 968 are in red. The peptide VLSPEAVR (SEQ ID NO: 3) is present in both isoforms whereas VSPESSDDTSTTVVYR (SEQ ID NO: 4) maps to the C-terminus unique to the mouse GAC (Accession #NP_001106854). GAC has a predicted molecular weight of 65,864.

FIG. 9A shows that the concentration of inorganic phosphate is kept constant at 150 mM and the concentration of glutamine was varied from 0 to 50 mM. FIG. 9B shows the data in FIG. 9A is shown as a double-reciprocal lineweaver-burke plot. FIG. 9C shows that the concentration of glutamine is kept constant at 20 mM and the concentration of inorganic phosphate has varied from 0 to 200 mM. The data are plotted as GA activity as function of varying concentrations of glutamine or inorganic phosphate. The data are the average of 3 experiments and are plotted as mean±SEM.

FIG. 10A shows that NIH 3I3 cells stably expressing Cdc42(F28L), cells stably expressing Cdc42 (F28L) transfected with control siRNA or siRNAs targeting both isoforms of mouse KGA, and control (vector) cells, are grown in soft agar and scored after 10 days. Histograms show the percentage of the total number of colonies greater than 50 μm in diameter. Data represent the average of 3 experiments (mean±s.d.). FIG. 10B shows that NIH 3T3 cells are transfected with control siRNA or siRNAs targeting both isoforms of mouse KGA, cultured in DMEM supplemented with 10% calf serum for the indicated number of days, and then are trypsinized and counted. FIG. 10B (top) shows histograms that represent the average of 3 experiments (mean±s.d.). FIG. 10B (bottom panel) shows the relative efficiencies of the siRNAs targeting KGA. FIG. 10C shows that the indicated breast cancer cell lines are transfected with control siRNA or with siRNAs targeting both isoforms of KGA and then grown in soft agar and scored after 10 days as described in S6A. Data represent the average of 3 experiments (mean±s.d.).

FIG. 11A shows that mitochondrial fractions from equivalent numbers of the indicated stable cell lines, treated or untreated with 10 μM 968, are assayed for GA activity in the presence of 133 mM inorganic phosphate (+Pi). The addition of Pi stimulated the GA activity in control 3T3 cells, Dbl-expressing cells, and Cdc42(F28L)-expressing cells by ~6-fold, 2-fold, and 3-fold, respectively. 100% represents the Pi-stimulated activity measured for Dbl-transformed cells that are not treated with 968. Data is the average of 3 experiments (±s.d.). FIG. 11B shows that mitochondrial fractions from equivalent numbers of the indicated cells, treated or untreated with 10 μM 968, are assayed for GA activity in the presence of 133 mM Pi. The addition of Pi stimulated the GA activity of HMECs, MDA-MB231 cells, and SKBR3 cells by ~5-fold, 2-fold, and 1.4-fold, respectively. 100% represents the Pi-stimulated activity for SKBR3 cells that were not treated with 968. Data are the average of 3 experiments (±s.d.). FIG. 11C (left) shows that SKBR3 cells are transfected with control siRNA or siRNAs targeting the RhoA and RhoC GTPases (i.e. a double knock-down). Mitochondrial fractions are prepared from equal numbers of cells and assayed for GA activity in the presence or absence of 133 mM Pi. The data are plotted as the percentage of GA activity measured for untreated SKBR3 cells and represent the average of 2 experiments. FIG. 11C (right) shows that the efficiencies of the siRNAs against RhoC and RhoA were assessed by Western blot analysis using anti-RhoA and anti-RhoC antibodies. FIG. 11D shows Pi-stimulated GA activity in mitochondrial fractions from NTH 3T3 cells stably expressing Dbl that were cultured for 2 days and treated or untreated with 2 μM BAY 11-7082, or transfected with control siRNA or siRNAs targeting the p65/RelA subunit. 100% represents the P1-stimulated activity measured for untreateDbl-transformed cells. The data represent the average of 2 experiments. FIG. 11E shows Pi-stimulated GA activity in the mitochondrial fractions from SKBR3 cells treated with 2 μM BAY 11-7082, or transfected with control siRNA or siRNAs targeting p65/RelA. 100% represents the Pi-stimulated activity for untreated SKBR3 cells. The data represent the average of 2 experiments.

DETAILED DESCRIPTION OF THE INVENTION

Figure 1A:
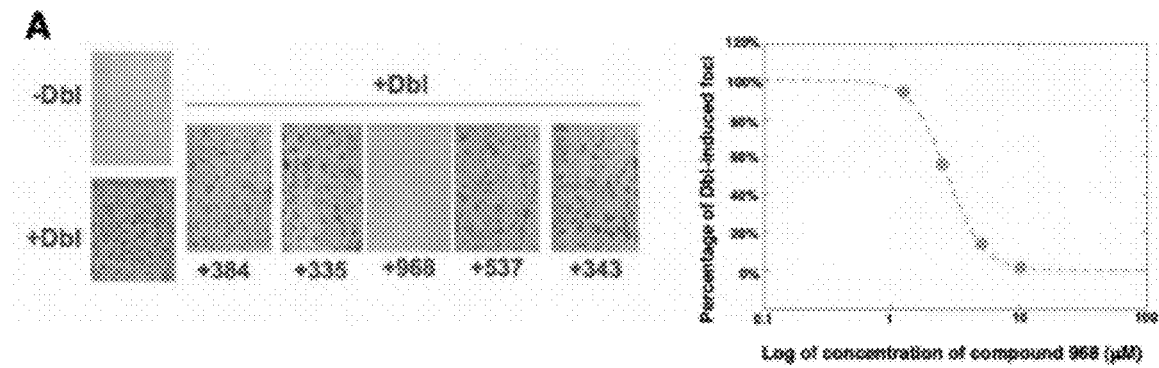

As used above, and throughout the description of this invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

The term "halo" or "halogen" means fluoro, chloro, bromo, or iodo.

The term "optionally substituted" indicates that a group may have a substituent at each substitutable atom of the group (including more than one substituent on a single atom), and the identity of each substituent is independent of the others.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent. Exemplary substitutents include, without limitation, oxo, thio (i.e. =S), nitro, cyano, halo, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_6$ cycloalkyl, $C_4$-$C_7$ cycloalkylalkyl, monocyclic aryl, monocyclic hetereoaryl, polycyclic aryl, and polycyclic heteroaryl.

The term "monocyclic" indicates a molecular structure having one ring.

The term "polycyclic" indicates a molecular structure having two or more rings, including, but not limited to, fused, bridged, or spiro rings.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "alkoxy" means an alkyl-O—, alkenyl-O—, or alkynyl-O— group wherein the alkyl, alkenyl, or alkynyl group is described above. Exemplary alkoxy groups include methoxy, ethoxy, n-propoxy, i-propoxy, n-butoxy, pentoxy, and hexoxy.

The term "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

The term "cycloalkylalkyl" refers to a radical of the formula —$R^a R^b$ where $R^a$ is an alkyl radical as defined above and $R^b$ is a cycloalkyl radical as defined above. The alkyl radical and the cycloalkyl radical may be optionally substituted as defined above.

The term "aryl" refers to aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" refers to a radical of the formula —$R^a R^b$ where $R^a$ is an alkyl radical as defined above and $R^b$ is an aryl radical as defined above. The alkyl radical and the cycloalkyl radical may be optionally substituted as defined above.

The term "aryarylalkyl" refers to a radical of the formula —$R^a R^b R^c$ where $R^a$ is an alkyl as defined above, $R^b$ is an aryl radical as defined above, and $R^c$ is an aryl radical as defined above. The alkyl radical and both aryl radicals may be optionally substituted as defined above.

The term "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, or a polycyclic ring system, which may include fused, bridged, or spiro ring systems; and the nitrogen, carbon, or sulfur atoms in the heterocyclyl radical may be optionally oxidized; the nitrogen atom may be optionally quaternized; and the ring radical may be partially or fully saturated. Examples of such heterocyclyl radicals include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

The term "heteroaryl" refers to an aromatic ring radical which consists of carbon atoms and from one to five heteroatoms selected from the group consisting of nitrogen, oxygen, and sulfur. For purposes of this invention the heteroaryl may be a monocyclic or polycyclic ring system; and the nitrogen, carbon, and sulfur atoms in the heteroaryl ring may be optionally oxidized; the nitrogen may optionally be quaternized. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl.

Further heterocycles and hetaryls are described in Katritzky et al., eds., "Comprehensive Heterocyclic Chemistry: The Structure, Reactions, Synthesis and Use of Heterocyclic Compounds," Vol. 1-8, Pergamon Press, N.Y. (1984), which is hereby incorporated by reference in its entirety.

The term "compounds of the present invention", and equivalent expressions are meant to embrace compounds of general Formulae (I), (II), and/or (III) (as well as compounds comprising their active moieties) as herein before described, which expression includes the prodrugs, the pharmaceutically acceptable salts, and the solvates, e.g., hydrates, where the context so permits. Similarly, reference to intermediates, whether or not they themselves are claimed, is meant to embrace their salts and solvates, where the context so permits. For the sake of clarity, particular instances, when the context so permits, are sometimes indicated in the text, but these instances are purely illustrative and it is not intended to exclude other instances when the context so permits.

The term "treatment" or "treating" means any manner in which one or more of the symptoms of a disease or disorder are ameliorated or otherwise beneficially altered. Treatment also encompasses any pharmaceutical use of the compositions herein, such as use for treating diseases or disorders mediated by the production of glutamate from glutamine.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

A first aspect of the present invention relates to a method of reducing the production of glutamate from glutamine in a cell or a tissue. The method involves inhibiting glutaminase C activity in the cell or tissue under conditions effective to reduce production of glutamate from glutamine.

Glutaminase C is the isoform-2 of the human glutaminase, an enzyme found in kidney and other tissues and generally referred as kidney-type glutaminase. Glutaminase C is involved in the hydrolysis of glutamine to glutamate and ammonium.

In one embodiment, this aspect of the present invention can be carried out by inhibiting overexpression-independent glutaminase C activity and/or inhibiting glutaminase C activity independent of exogenous phosphate addition. Alternatively, an activating phosphorylation event on glutaminase C can be inhibited. As a further alternative of the method of the present invention, inhibition of glutaminase C activity can be performed by inhibiting glutaminase C hyperactivity.

Although glutaminase C expression has been found to be increased in some cancers, applicants have found that the participation of GAC is not limited to an increase in expression. Some cancer cells (such as the breast cancer cell line, SKBR3) have been found to exhibit GAC expression levels which are similar to normal cells, but are still dependent on the presence of GAC for cell growth (see FIG. 3C). Thus, by reducing the normal expression levels of GAC, one can inhibit GAC activity in cancer cells.

Figure 11:
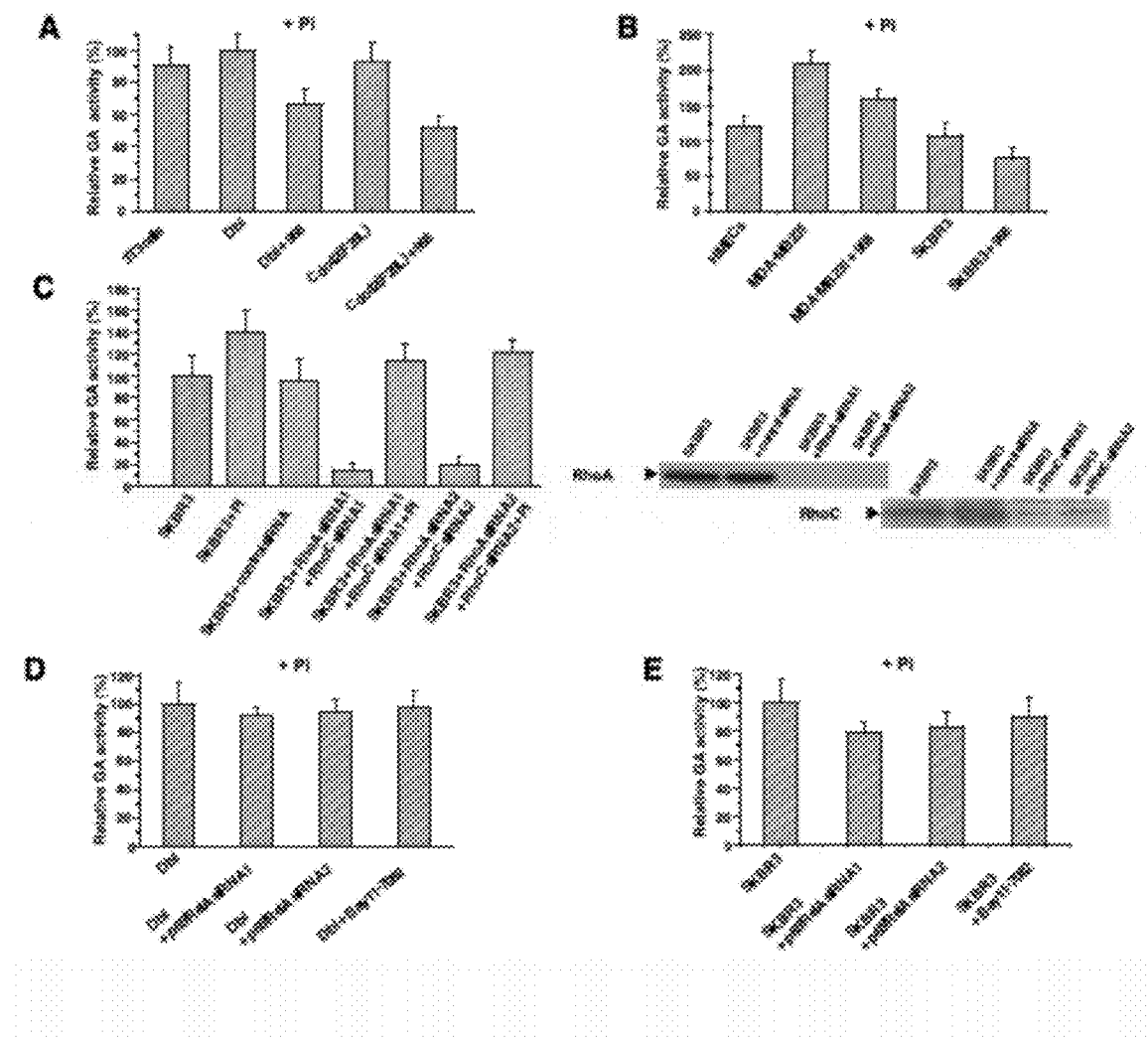
FIGS. 11A-E illustrate the effects of different treatments on GA activity.

GAC isolated from cancer cells can show an elevated glutaminase activity level relative to GAC isolated from normal cells when assayed in the absence of phosphate, but in the presence of phosphate the enzymes isolated from both normal and cancer cells show a similar extent of activation per amount of GAC (FIG. 3G and FIG. 11B). Thus, the GAC in cancer cells is not dependent on the exogenous addition of phosphate to be active. Inhibition of the phosphate-independent activation of GAC in cancer cells would inhibit the production of glutamate from glutamine.

One way in which the GAC activity from cancer cells may be increased relative to the GAC activity in normal cells is by a phosphorylation event that occurs on GAC. If the phosphorylations on GAC are removed/blocked using either alkaline phosphate or a small molecule (e.g., compound 968 in FIG. 1C), the ability for GAC to produce glutamate from glutamine is limited.

The activation state of GAC may vary among different cancer cells, regardless of the expression levels of GAC. A higher amount of activity may be referred to as "hyperactivity". For example, Dbl transformed cells and Cdc42 F28L transformed cells contain similar levels of GAC as do untransformed NIH 3T3 cells. However, the GAC in the Dbl and Cdc42 transformed cells shows a higher activation than in the non-transformed cells, with the GAC from the Dbl cells being approximately twice as active than the GAC from the Cdc42 transformed cells (FIG. 3F). Thus, the GAC in the Dbl transformed cells is hyperactive. Inhibiting the hyperactivity of GAC in Dbl cells would limit the production of glutamate from glutamine by glutaminase C.

In another embodiment of this aspect of the present invention, the method of inhibiting involves providing a compound selected from the group consisting of:

(i) a compound of formula (I):

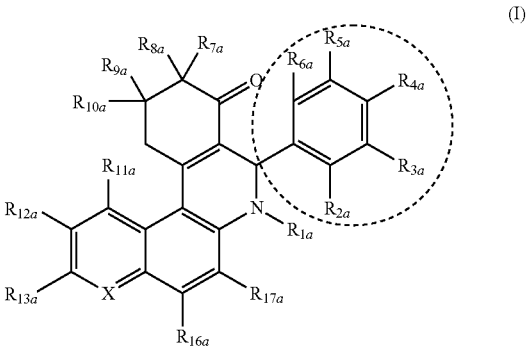

wherein:

the dotted circle identifies an active moiety;

X is independently —$CR_{14a}$— or N;

$R_{1a}$ is independently H, OH, $OR_{14a}$, $C_1$-$C_6$ alkyl, $C_2$-$C_6$ alkenyl, $C_2$-$C_6$ alkynyl, $R_{14a}C(O)$—, $R_{14a}C(O)$—, $R_{14a}S(O)$—, or $R_{14a}S(O)_2$—;

$R_{2a}$, $R_{3a}$, $R_{4a}$, $R_{5a}$, and $R_{6a}$ are each independently H, halogen, $NO_2$, OH, $OR_{14a}$, —$SR_{14a}$, $NH_2$, $NHR_{14a}$, $NR_{14a}R_{15a}$, $R_{14a}C(O)$—, $R_{14a}OC(O)$—, $R_{14a}C(O)O$—, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen; or $R_{2a}$ and $R_{3a}$, $R_{3a}$ and $R_{4a}$, $R_{4a}$ and $R_{5a}$, or $R_{5a}$ and $R_{6a}$ can combine to form a heterocyclic ring;

$R_{7a}$, $R_{8a}$, $R_{9a}$, and $R_{10a}$ are each independently H, OH, $NH_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen, wherein the aryl, heteroaryl, and aryl $C_1$-$C_6$ alkyl are optionally substituted from 1 to 3 times with substituents selected from the group consisting of halogen, OH, $NH_2$, $C_1$-$C_6$ alkyl, $C_2$-$C_6$ alkenyl, $C_1$-$C_6$ alkoxy, SH, and $C_1$-$C_6$thioalkyl; and $R_{11a}$, $R_{12a}$, $R_{13a}$, $R_{14a}$, $R_{15a}$, $R_{16a}$, and $R_{17a}$ are each independently H, halogen, OH, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, each one of $R_{11a}$-$R_{17a}$ optionally substituted with $NH_2$, OH, halogen, COOH, $NO_2$, and CN;

(ii) a compound of formula (II):

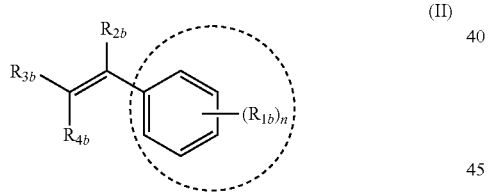

(II)

wherein:

the dotted circle identifies an active moiety;

n is an integer from 1 to 4;

$R_{1b}$ is independently at each occurrence H, OH, $OR_{5b}$, halogen, CN, $NO_2$, $NH_2$, $NHR_{5b}$, $NR_{5b}R_{6b}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen;

$R_{2b}$ is independently H, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or mono or polycyclic aryl;

$R_{3b}$ and $R_{4b}$ are independently H, $OR_{5b}$, $SR_{5b}$, $R_{5b}S(O)$—, $R_{5b}S(O)_2$—, —$COOR_{5b}$, —$C(O)NR_{5b}R_{6b}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen; or $R_{3b}$ and $R_{4b}$ can combine together to form a mono or polycyclic heterocyclyl or heteroaryl containing from 1-5 heteroatoms selected from the group consisting of nitrogen, sulfur, and oxygen, each formed heteroaryl or heterocyclyl optionally substituted with substituents selected from the group consisting of oxo, thio, amino, $C_1$-$C_6$ alkyl, $C_2$-$C_6$ alkenyl, and $C_2$-$C_6$ alkynyl; and $R_{5b}$ and $R_{6b}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen, each one of $R_{5b}$, or $R_{6b}$ optionally substituted from 1 to 3 times with substituents selected from the group consisting of H, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl;

(iii) a compound of formula (III):

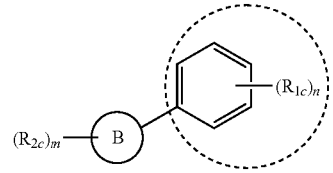

(III)

wherein:

the dotted circle identifies an active moiety;

m and n are integers from 1 to 4;

B is a substituted or unsubstituted mono or polycyclic aryl or mono or polycyclic heterocyclyl or heteroaryl with each cyclic unit containing from 1 to 5 heteroatoms selected from the group consisting of nitrogen, sulfur, and oxygen;

$R_{1c}$ and $R_{2c}$ are independently H, OH, $OR_{3c}$, halogen, CN, $NO_2$, COOH, $NH_2$, $NHR_{3c}$, $NR_{3c}R_{4c}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen; and $R_{3c}$ and $R_{4c}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen; and (iv) a compound comprising the active moiety of formula I, formula II, or formula III. Glutaminase C is then contacted with the compound under conditions effective to reduce the production of glutamate from glutamine in a cell or a tissue.

The compounds described in the present invention may further comprise an active moiety (linkable to other moieties), where the active moiety has the formula:

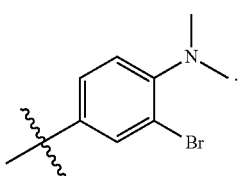 [SMILES: *c1ccc(N(C)C)c(Br)c1]
Exemplary compounds of the present invention include any of the following:
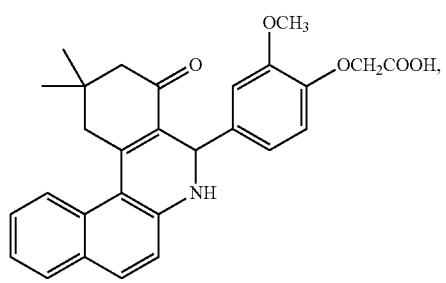
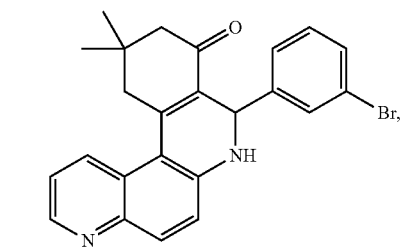
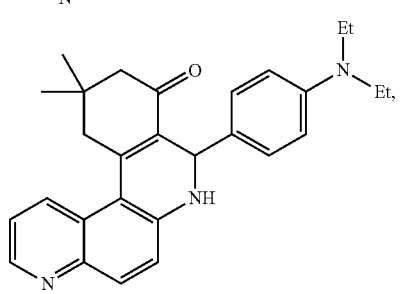
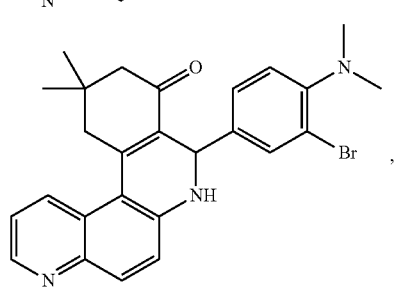
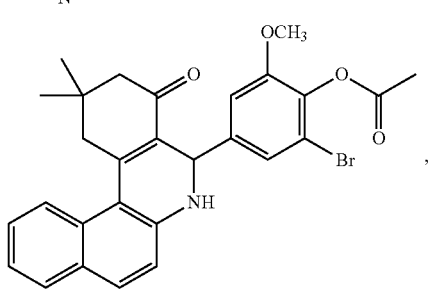
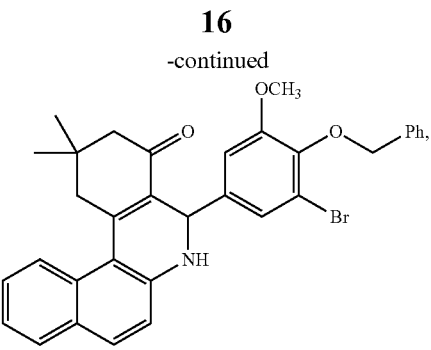
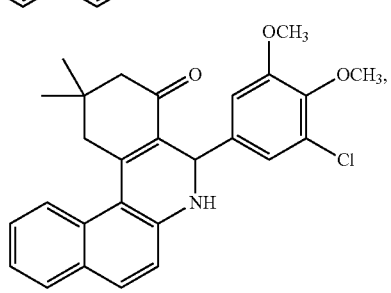
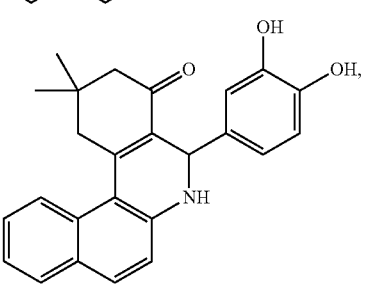
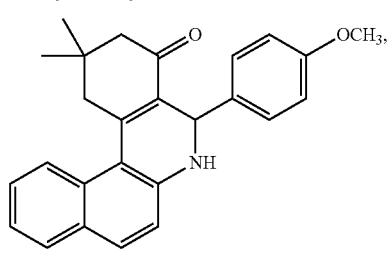
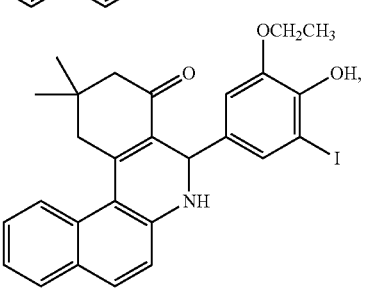
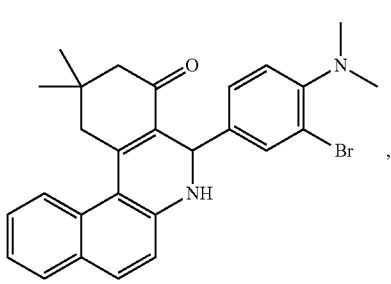

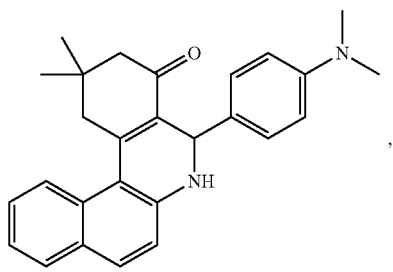,
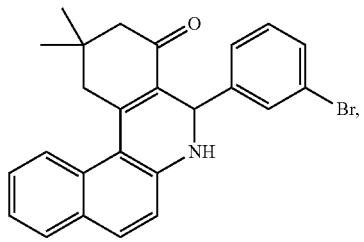,
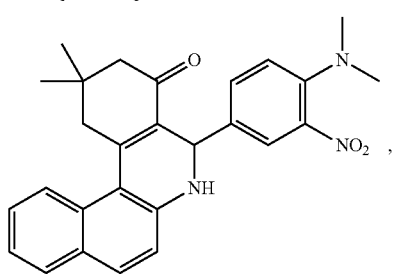,
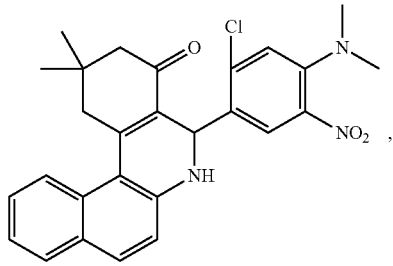,
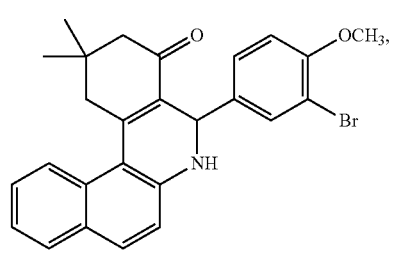,
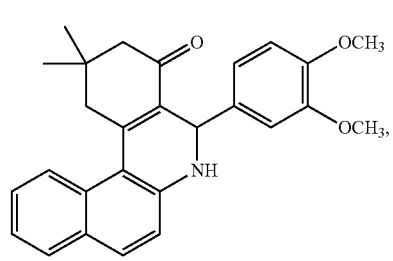,
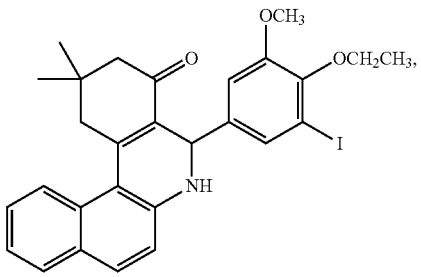,
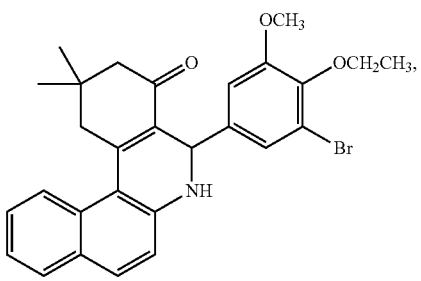,
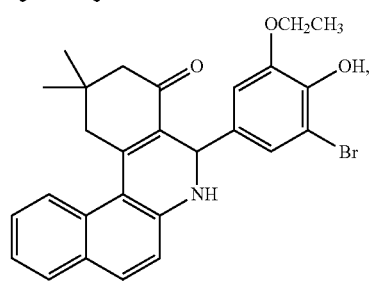,
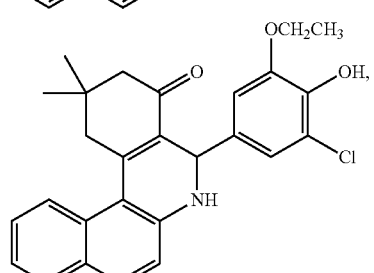,
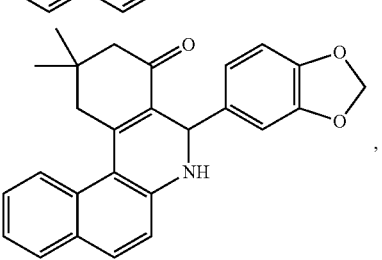,
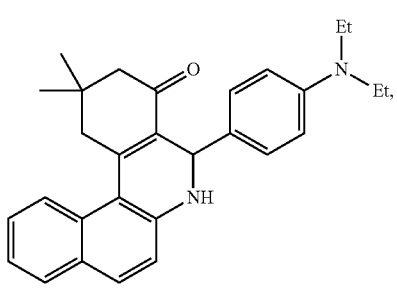,

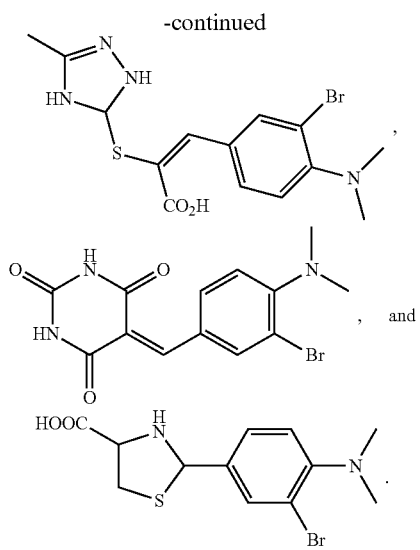

Another aspect of the present invention relates to a method of treating a subject with a condition mediated by production of glutamate from glutamine. The method involves selecting a subject with a condition mediated by production of glutamate from glutamine by glutaminase C and administering to said selected subject an inhibitor of glutaminase C activity under conditions effective to treat the condition mediated by production of glutamate from glutamine.

The inhibitor according to this aspect of the present invention may be an inhibitor of expression-independent glutaminase C activity and/or an inhibitor of glutaminase C activity independent of exogenous phosphate addition. Alternatively, phosphorylation of glutaminase C can be inhibited.

This treatment can be carried out for the benefit of humans or animals (e.g. rat, mice, pigs, horses, monkeys, cows, sheep, guinea pigs, dogs, and cats).

Suitable examples of such inhibitors include any of the compounds described above.

The compounds of the present invention can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The compounds of the present invention (e.g., formulae I, II, and/or III (as well as compounds comprising their active moieties)) can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682, which is hereby incorporated by reference in its entirety) via a liposomal formulation (see, e.g., European Patent No. 736299, WO 99/59550, and WO 97/13500, which are hereby incorporated by reference in their entirety), via formulations described in WO 03/094886, which is hereby incorporated by reference in its entirety, or in some other form. The compounds of the present invention can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al., Nature Reviews Drug Discovery 3:115 (2004), which is hereby incorporated by reference in its entirety). The compounds can be administered locally, for example, at the site of injury to an injured blood vessel. The compounds can be coated on a stent. The compounds can be administered using high-velocity transdermal particle injection techniques using the hydrogel particle formulation described in U.S. Patent Publication No. 20020061336, which is hereby incorporated by reference in its entirety. Additional particle formulations are described in WO 00/45792, WO 00/53160, and WO 02/19989, which are hereby incorporated by reference in their entirety. An example of a transdermal formulation containing plaster and the absorption promoter dimethyl-isosorbide can be found in WO 89/04179, which is hereby incorporated by reference in its entirety. WO 96/11705, which is hereby incorporated by reference in its entirety, provides formulations suitable for transdermal administration.

The condition mediated by production of glutamate from glutamine include, without limitation, breast cancer, lung cancer, brain cancer, pancreatic cancer, and colon cancer.

Another aspect of the present invention relates to a pharmaceutical composition comprising a compound selected from the group consisting of:

(i) a compound of formula (II):

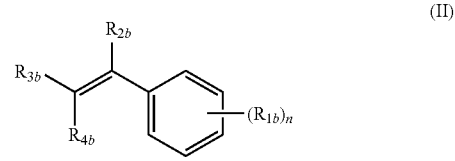

(II)

wherein:

n is an integer from 1 to 4;

$R_{1b}$ is independently at each occurrence H, OH, $OR_{5b}$, halogen, CN, $NO_2$, $NH_2$, $NHR_{5b}$, $NR_{5b}R_{6b}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen;

$R_{2b}$ is independently H, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, or mono or polycyclic aryl;

$R_{3b}$ and $R_{4b}$ are independently H, $OR_{5b}$, $SR_{5b}$, $R_{5b}S$(O)—, $R_{5b}S(O)_2$—, —$COOR_{5b}$, —C(O)$NR_{5b}R_{6b}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen; or $R_{3b}$, and $R_{4b}$ can combine together to form a mono or polycyclic heterocyclyl or heteroaryl containing from 1-5 heteroatoms selected from the group consisting of nitrogen, sulfur, and oxygen, each formed heteroaryl or heterocyclyl optionally substituted with substituents selected from the group consisting of oxo, thio, amino, $C_1$-$C_6$ alkyl, $C_2$-$C_6$ alkenyl, and $C_2$-$C_6$ alkynyl; and $R_{5b}$ and $R_{6b}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen, each one of $R_{5b}$ or $R_{6b}$ optionally substituted from 1 to 3 times with substituents selected from the group consisting of H, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl;

(ii) a compound of formula (III):

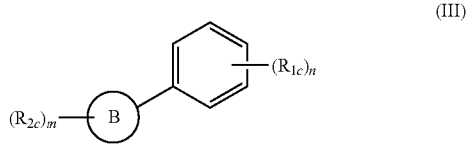

(III)

wherein:
m and n are integers from 1 to 4;
B is a substituted or unsubstituted mono or polycyclic aryl or mono or polycyclic heterocyclyl or heteroaryl with each cyclic unit containing from 1 to 5 heteroatoms selected from the group consisting of nitrogen, sulfur, and oxygen;
$R_{1c}$ and $R_{2c}$ are independently H, OH, $OR_{3c}$, halogen, CN, $NO_2$, COOH, $NH_2$, $NHR_3$, $NR_3R_{4c}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen; and
$R_{3c}$ and $R_{4c}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen; and (iii) a compound comprising the active moiety of formula II or formula III.

According to this aspect of the present invention, the pharmaceutical compositions can comprise a compound of the present invention and a pharmaceutically acceptable carrier and, optionally, one or more additional active agent (s) as discussed below.

The amount of active ingredient that may be combined with the carrier materials to produce a single dosage form will vary depending upon the host treated and the particular mode of administration. For example, a formulation intended for the oral administration of humans may vary from about 5% to about 95% of the total composition. Dosage unit forms will generally contain between from about 1 mg to about 500 mg of active ingredient.

Any pharmaceutically acceptable liquid carrier suitable for preparing solutions, suspensions, emulsions, syrups and elixirs may be employed in the composition of the invention. Compounds of the present invention may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Pharmaceutically acceptable salts include, but are not limited to, amine salts, such as but not limited to, N, N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methyl-benzimidazole, diethylamine and other alkylamines, piperazine, and tris (hydroxymethyl) aminomethane; alkali metal salts, such as but not limited to, lithium, potassium, and sodium; alkali earth metal salts, such as but not limited to, barium, calcium, and magnesium; transition metal salts, such as but not limited to, zinc; and other metal salts, such as but not limited to, sodium hydrogen phosphate and disodium phosphate; and also including, but not limited to, salts of mineral acids, such as but not limited to, hydrochlorides and sulfates; and salts of organic acids, such as but not limited to, acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C=C (OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C=C (OC(O) R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3, or 4, solvent or water molecules.

It will be understood, however, that the specific dose level for any particular patient will depend upon a variety of factors, including the activity of the specific compound employed, the age, body weight, general health, sex, diet time of administration, route of administration, rate of excretion, drug combination and the severity of the particular disease undergoing therapy.

All methods comprise administering to the subject in need of such treatment an effective amount of one or more compounds of the present invention.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the present invention can be administered alone or as an active ingredient of a formulation. Thus, the present invention also includes pharmaceutical compositions of one or more compounds of formulae I, II, and/or III (as well as compounds comprising their active moieties) containing, for example, one or more pharmaceutically acceptable carriers. The compounds of the present invention can be administered in a form where the active ingredient is substantially pure.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition), which are hereby incorporated by reference in their entirety.

Yet another aspect of the present invention relates to a compound of formula:

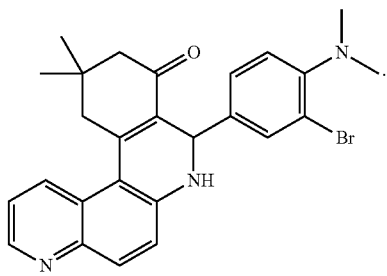 [SMILES: CN(C)c1ccc(C2Nc3ccc4ncccc4c3C3=C2C(=O)CC(C)(C)C3)cc1Br]

Another aspect of the present invention relates to the method of screening for compounds capable of reducing the production of glutamate from glutamine. The method involves providing a cell or tissue under conditions effective for the cell or tissue to produce glutamate from glutamine as a result of glutaminase C activity. A plurality of candidate compounds is provided to contact the cell or tissue and the candidate compounds which inhibit glutaminase C activity as a result of said contacting is identified.

In one embodiment of this aspect of the present invention, glutaminase C activity refers to phosphorylation of glutaminase C.

EXAMPLES

The Examples set forth below are for illustrative purposes only and are not intended to limit, in any way, the scope of the present invention.

Example 1—Identification of Glutaminase as the Target of 968

Compound 968 (5-[3-bromo-4-(dimethylamino)phenyl]-2,2-dimethyl-2,3,5,6-tetrahydrobenzo[a]) was obtained from SPECS (Netherlands; CAS registry #311795-38-7). In order to identify the molecular target of 968, its active moiety (3-bromo-4-(dimethylamino)benzyl) (See FIG. 1C) (ChemBridge Corporation, San Diego; CAS registry #56479-63-1) was incorporated into biotin hydrazide by reacting 3-bromo-4-(dimethylamino)benzaldehyde or formaldehyde (as a negative control) at a 5-fold molar excess overnight at 42° C., followed by reduction with cyanoborohydride coupling buffer. The 968-biotin adduct (MW=554 Da) was confirmed by mass spectrometry and incubated with streptavidin-agarose beads equilibrated with cell lysis buffer (5 μM MgCl$_2$, 120 μM NaCl, 10 μM HEPES, pH 7.4, 0.5% NP-40, 10 mg/ml leupeptin, and 10 mg/ml aprotinin) prior to incubation with lysates from NIH 3T3 cells stably expressing Cdc42(F28L) (5 ml containing ~2 mg/ml total protein) for 2 h at 4° C. The beads were washed 3× with cold lysis buffer and pelleted by centrifugation and the associated proteins were resolved by SDS-PAGE. A silver-stained protein band ($M_r$~66 kDa) that bound specifically to the 968-biotin beads and not to the control beads was excised and analyzed by mass spectrometry at the Harvard Microchemistry Facility (Cambridge, Mass.) and identified as mouse KGA isoform-2 (accession number NP_001106854), the mouse ortholog of the human GAC isoform.

Example 2—Mitochondrial Preparations

Mitochondrial preparations were obtained using the mitochondria isolation kit from QIAGEN (Cat #37612). A suspension containing 2×10$^7$ cells was transferred into a 50 ml conical tube and centrifuged at 500×g for 10 minutes at 4° C. The pellets were resuspended in 2 ml of ice-cold lysis buffer (supplied by QIAGEN) and incubated for 10 minutes at 4° C. using an end-over-end shaker. The lysates were centrifuged at 1000×g for 10 minutes at 4° C., and the pellets were resuspended in a buffer supplied by the manufacturer and disrupted completely by using a blunt-ended, 23-gauge needle and a syringe, followed by centrifugation at 6000×g for 20 minutes at 4° C. The pellets were resuspended in 100 ml of 20 μM Hepes, pH 7.4, 150 μM NaCl, 1% NP-40, 20 μM b-glycerolphosphate, 1 μM sodium orthovanadate, and 20 μM sodium fluoride and assayed for GA activity as previously described (Kenny et al., "Bacterial Expression, Purification and Characterization of Rat Kidney-Type Mitochondrial Glutaminase," *Protein Expr. Purif* 31:140-148 (2003), which is hereby incorporated by reference in its entirety) and further outlined below for assaying recombinant enzyme, except that the recombinant protein was replaced by 20 μl of resuspended mitochondrial lysate.

Example 3—RNAI

All knock-downs were performed by using Stealth Select RNAi Duplexes from Invitrogen that were transiently transfected into cells using Lipofectamine 2000. A non-specific oligonucleotide was used as a negative control. The relative knock-down efficiencies were determined using the following antibodies: A polyclonal antibody that recognizes both isoforms of KGA, an anti-RhoC polyclonal antibody from Santa Cruz, an anti-RhoA monoclonal antibody, and an anti-p65/RelA polyclonal antibody from Cell Signaling.

Example 4—Assays of Recombinant Glutaminase Activity

Glutaminase activity assays were performed on recombinant enzyme as previously described (Kenny et al., "Bacterial Expression, Purification and Characterization of Rat Kidney-Type Mitochondrial Glutaminase," *Protein Expr. Purif* 31:140-148 (2003), which is hereby incorporated by reference in its entirety). A plasmid encoding mouse GAC (residues 128-603) was cloned into the pET28a vector and the protein was expressed with an N-terminal histidine (His)-tag. The tag was cleaved using thrombin and the protein was further purified by anion-exchange and gel-filtration chromatography. Recombinant GAC (1 μM) was incubated with varying concentrations of 968 in 57 μM Tris-Acetate (pH 8.6) and 0.225 μM EDTA by rotating at 37° C. for 30 minutes, in a final volume of 80 μl. Compound 968 was diluted in DMSO such that the volume added was constant (5 μl) for all samples, ensuring that the concentration of DMSO (6.3% v/v) was the same in each of the assay incubations. A glutamine solution was then added to give a final volume of 115 μl and a final concentration of 17 μM. The reaction proceeded at 37° C. for 1 h and was stopped by adding 10 μl of ice-cold 3M HCl. An aliquot of the quenched reaction mixture (10 μl) was added to an incubation containing 114 μM Tris-HCl (pH 9.4), 0.35 μM ADP, 1.7 μM NAD and 6.3 U/ml glutamate dehydrogenase to give a final volume of 228 μl. The reaction mixture was incubated at room temperature for 45 minutes and the absorbance at 340 nm was recorded for each sample against a water blank. The absorbance of the sample with just the cocktail mixture was subtracted from each reading to calculate the activity of the enzyme.

Example 5—Glutaminase C Expression

Figure 12:
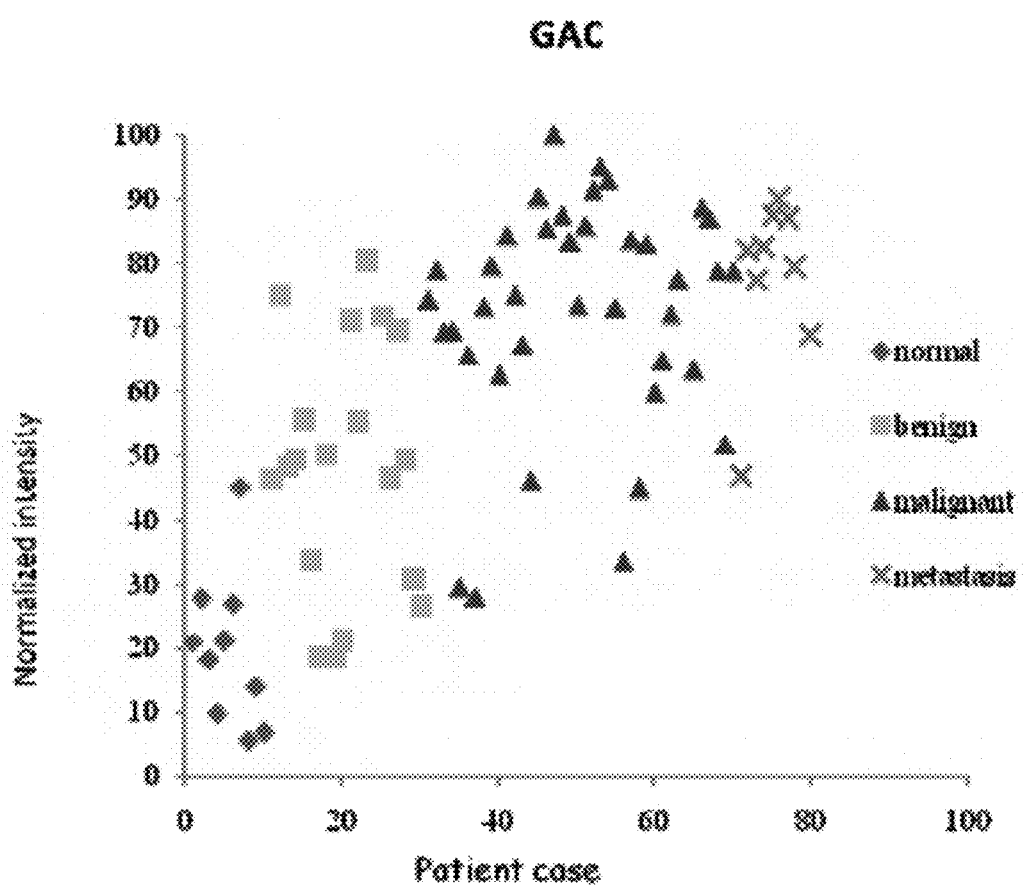
FIG. 12 illustrates GAC expression levels in normal and cancerous breast tissues obtained from 80 patients.

Serial slides of a breast tissue array were obtained from Biomax U.S.A. and were probed with either an antibody against GAC, or an antibody against actin (control). The expression of GAC was then normalized to the expression of actin for each sample. An increase in GAC protein levels were observed in transformed breast tissues. See FIG. 12.

Example 6—Comparison of Glutaminase C and Kidney-Glutaminase Expression

Figure 13:
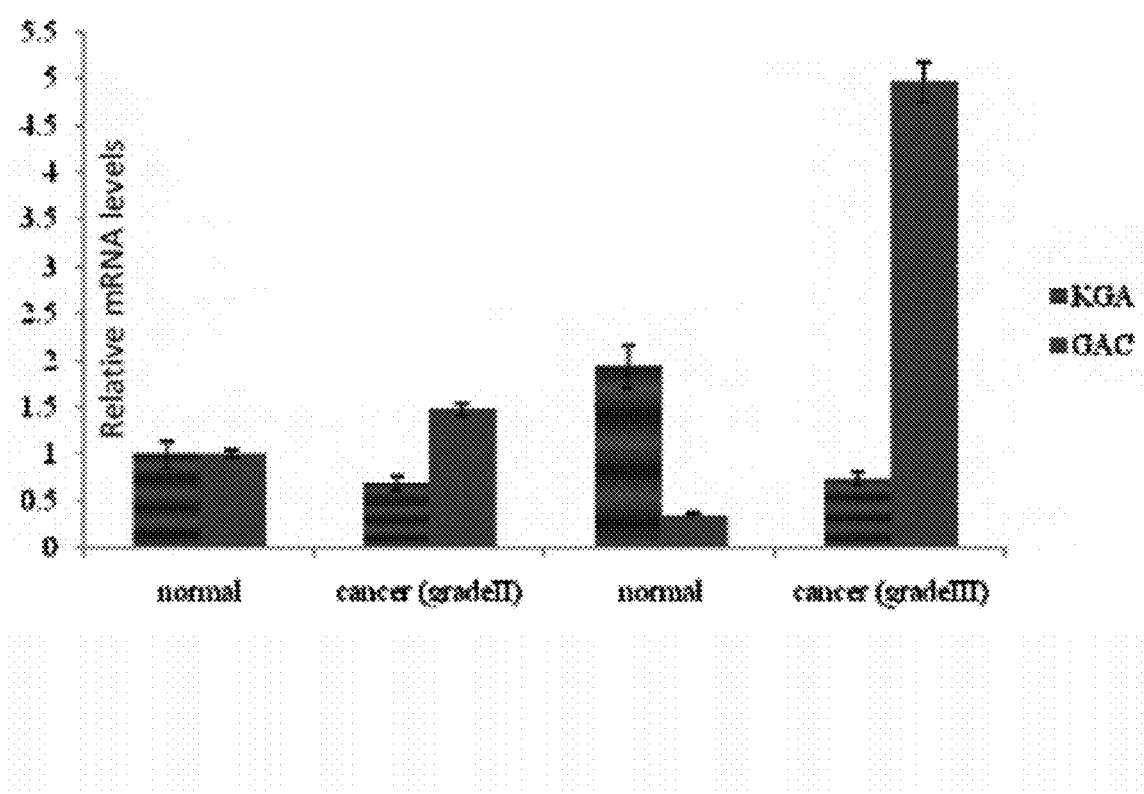
FIG. 13 shows that GAC, but not KGA, mRNA levels are increased in higher grade breast tumors.
Figure 14:
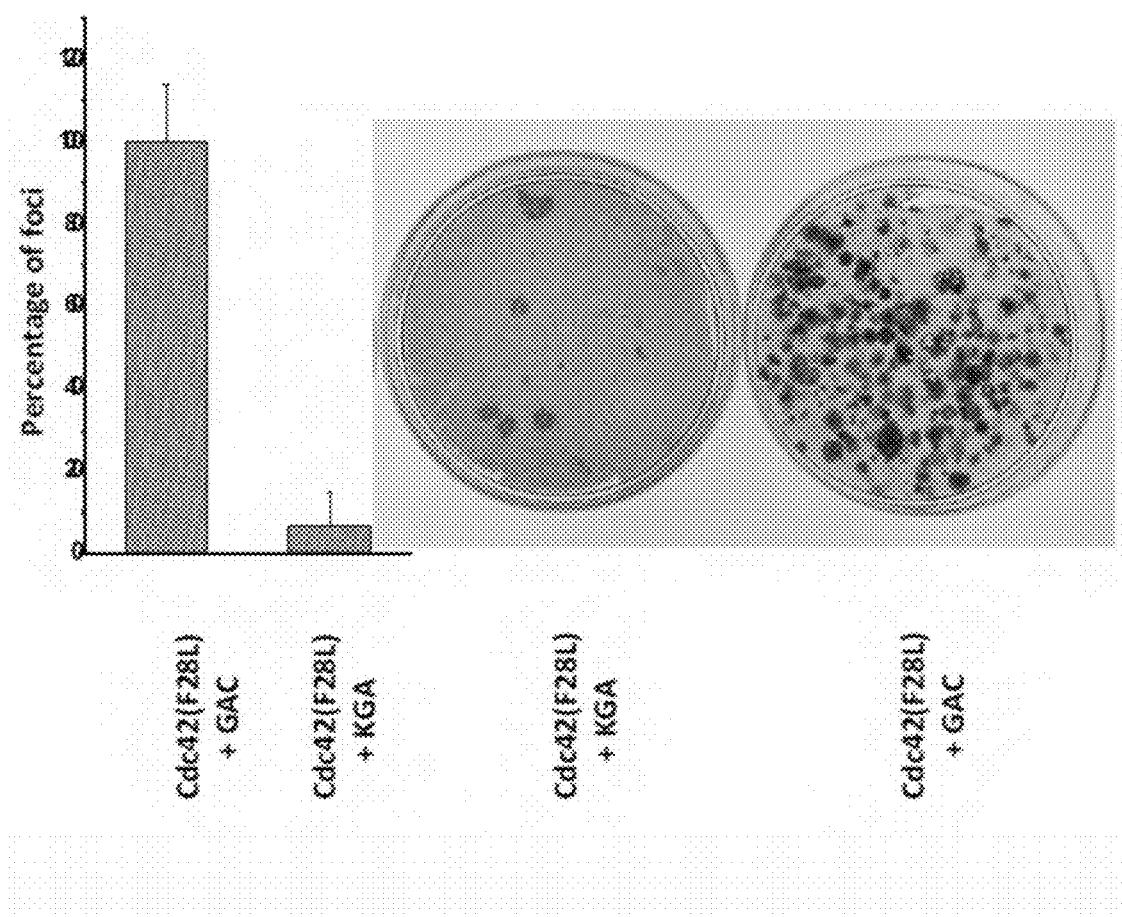
FIG. 14 shows that GAC, but not KGA, enhances the oncogenic potential of Cdc42.

Total RNA was extracted from normal or cancerous breast tissues, and complementary DNA was then synthesized. Quantitative PCR (qPCR) was performed in triplicate using primer sets to amplify KGA, GAC or GAPDH, the normalizer/housekeeping gene, on an AB17500 Fast Real-Time PCR System. Relative quantification studies were performed with the ABI7500 Fast System Sequence Detection Software. See FIG. 13.
NIH 3T3 cells expressing a constitutively active form of Cdc42, Cdc42 (F28L), were transiently transfected with either DNA encoding GAC or KGA. The cells were then allowed to grow under conditions permissive for focus formation and the number of foci were then counted and scored. See FIG. 14.

Example 7—Glutaminase C Phosphorylation

Figure 15:
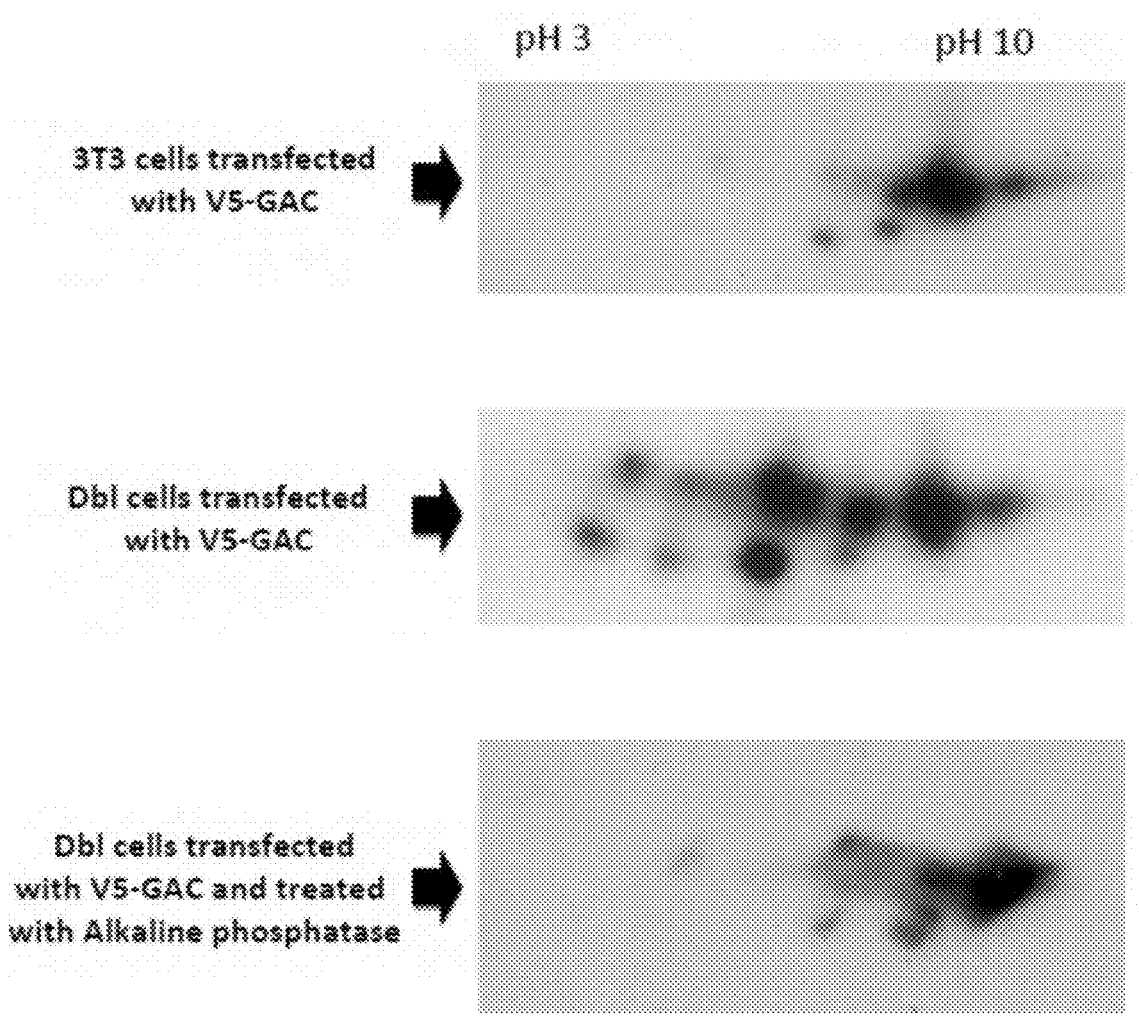
FIG. 15 illustrates that GAC is differentially phosphorylated in transformed (Dbl) cells but not in normal NIH 3T3 cells.

NIH 3T3 cells or NIH 3T3 cells stably expressing the Dbl oncogene, were transiently transfected with DNA encoding a VS-tagged GAC. The cells were then harvested, and the ectopically expressed GAC was isolated by immunoprecipitation via the V5 tag. The V5-GAC obtained from one of the Dbl samples was additionally treated with alkaline phosphatase under dephosphorylation conditions. The samples were then subjected to 2-D gel analysis to separate the V5-GAC by charge and size, and the V5-tagged GAC was visualized by Western blotting using an anti-V5 antibody. Multiple modification states of GAC were detected on GAC isolated from NIH 3T3 cells expressing Dbl as compared to the GAC isolated from untransformed NIH 3T3 cells. The multiple modification states of GAC were reversed when the protein was treated with alkaline phosphatase, suggesting that the modifications are phosphorylations. See FIG. 15.

Figure 16:
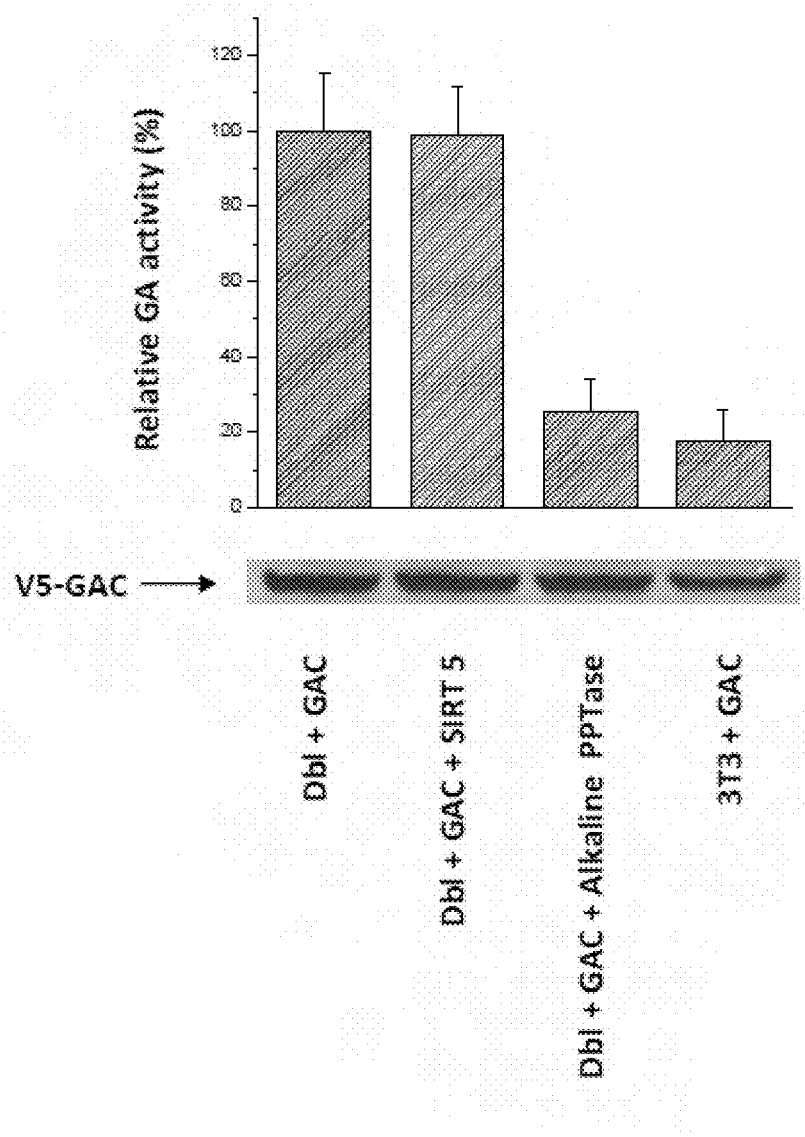
FIG. 16 illustrates that the phosphorylation of GAC is necessary for its basal glutaminase activity.

Example 8—Relationship of Glutaminase C Phosphorylation to Basal Glutaminase Activity NIH 3T3 cells or NIH 3T3 cells stably expressing the Dbl oncogene, were transiently transfected with DNA encoding a V5-tagged GAC. The cells were then harvested and the ectopically expressed GAC was isolated by immunoprecipitation via the V5 tag. The VS-GAC obtained from one of the Dbl samples was additionally treated with alkaline phosphtase under dephosphorylation conditions. See FIG. 16. The samples were then assayed for glutaminase activity in the absence of phosphate (top panel) and the relative expression levels of VS-GAC was determined by Western blotting using an anit-V5 antibody (bottom panel). The dephosphorylation of GAC isolated from Dbl cells resulted in a 75% reduction of basal glutaminase (phosphate independent) activity.

Example 9—Inhibition of Glutaminase C Phosphorylation by Compound 968

Figure 17:
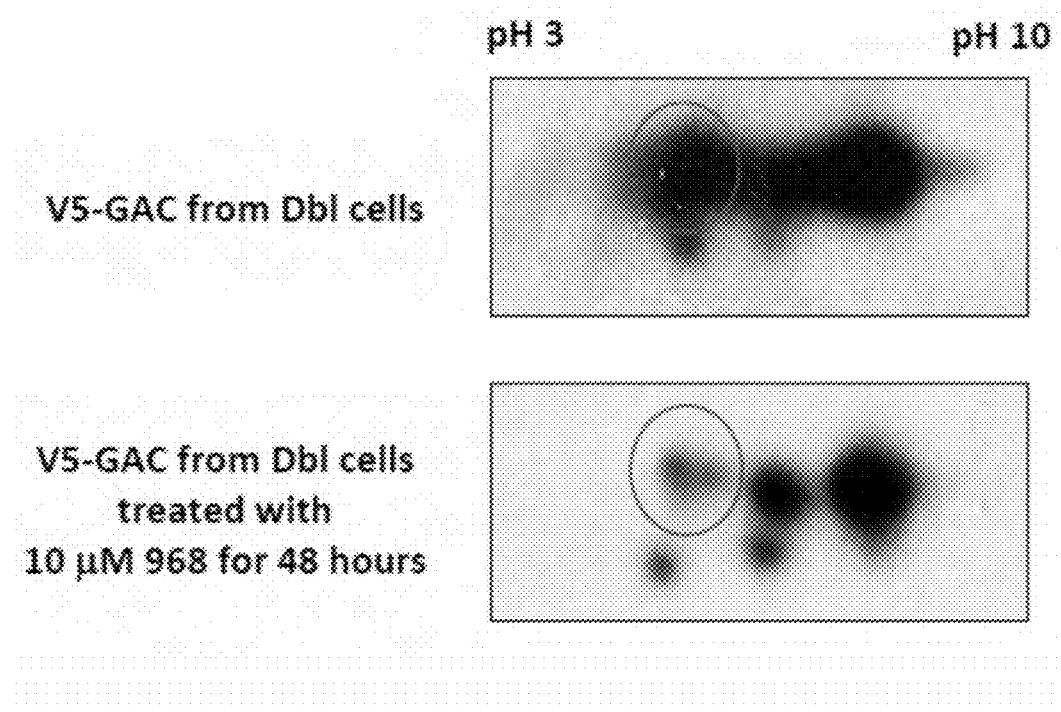
FIG. 17 illustrates that 968 treatment of cells inhibits the formation of at least one phosphorylation on GAC.

NIH 3T3 cells stably expressing the Dbl oncogene, were transiently transfected with DNA encoding a VS-tagged GAC, and then one sample was treated with 968 (10 μM) for 48 hours. The cells were then harvested and the ectopically expressed GAC was isolated by immunoprecipitation via the V5 tag. The samples were then subjected to 2-D gel analysis to separate the V5-GAC by charge and size, and the V5-tagged GAC was visualized by Western blotting using an anti-V5 antibody. The treatment of cells with 968 resulted in the significant reduction of at least one phosphorylation state of GAC. Since 968 inhibits the enzymatic activity of GAC, and the phosphorylation appears to be required for its basal enzyme activity, it appears that 968 might be functioning to inhibit glutaminase C by inhibiting the ability of at least one site on glutaminase C to become phosphorylated. See FIG. 17.

Example 10—Effect of Compound 968 on Oncogenic Growth

Figure 18:
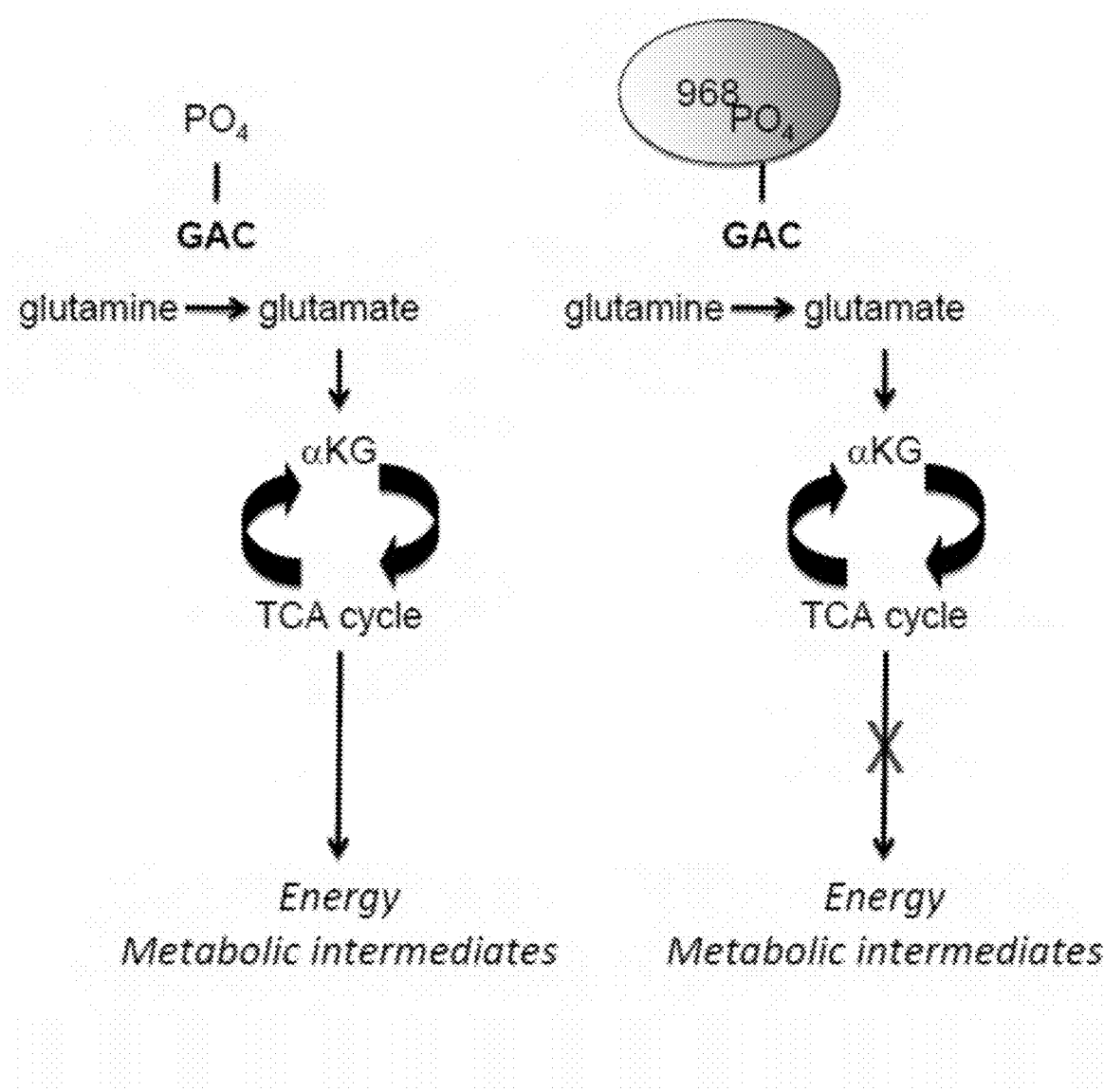
FIG. 18 illustrates a model for the mode of action of 968 on GAC and oncogenic growth.

In cancer cells, GAC undergoes a phosphorylation event (s) which in not observed in nontransformed cells (left panel). This phosphorylation leads to a phosphate-independent (basal) activation of GAC, resulting in a rise in glutamate production which feeds the TCA cycle to supply the cancer cell with the energy and metabolic intermediates it needs to support tumorogenic growth. It is proposed that 968 may function by blocking a tumor-specific phosphorylation event on GAC which is necessary for its phosphate-independent activity (right panel). The inhibition of GAC reduces the influx of glutamate into the TCA cycle and, thus, effectively "starves" the tumor cell of needed energy and metabolic intermediates. See FIG. 18.

Example 11—Inhibition of GAC (glutaminase C) Activity by Compound 968 and B-968

Figure 19:
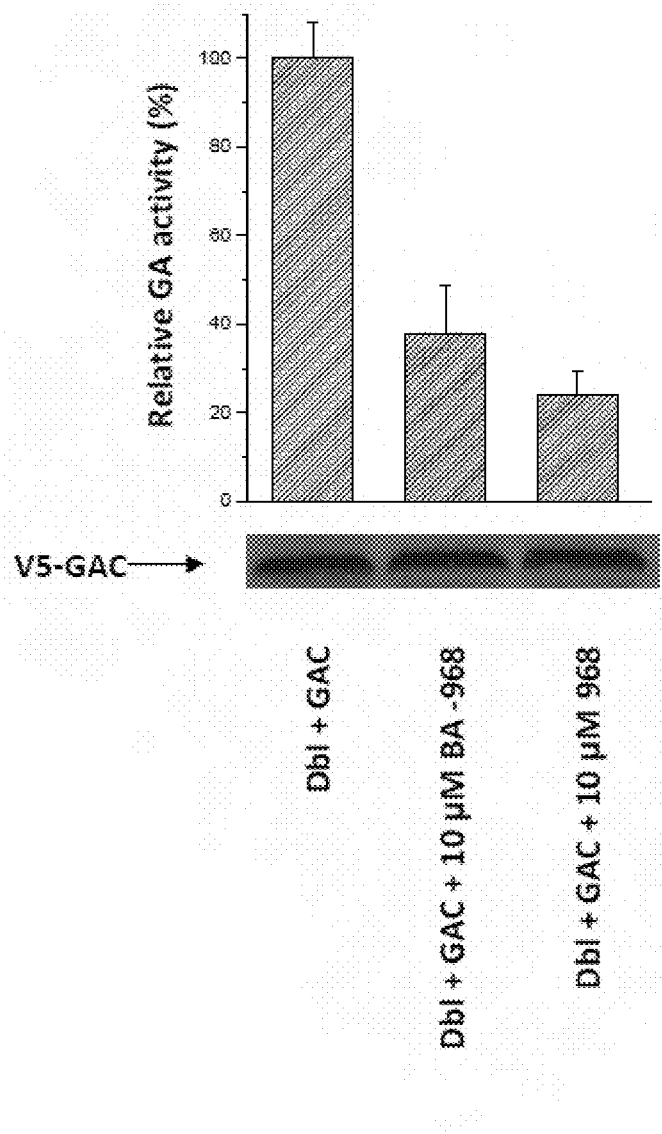
FIG. 19 illustrates both 968 and BA-968 are effective inhibitors of GAC activity.

NIH 3T3 cells stably expressing oncogenic Dbl were transiently transfected with DNA encoding VS-tagged GAC, and cells were treated with either 968 or BA-968 (10 mM) as indicated for 48 hours. The cells were then harvested and the ectopically expressed GAC was isolated by immunoprecipitation via the V5 tag. See FIG. 19. The samples were then assayed for glutaminase activity in the absence of phosphate (top panel) and the relative expression levels of VS-GAC was determined by Western blotting using an anti-V5 antibody (bottom panel).

Figure 1B:
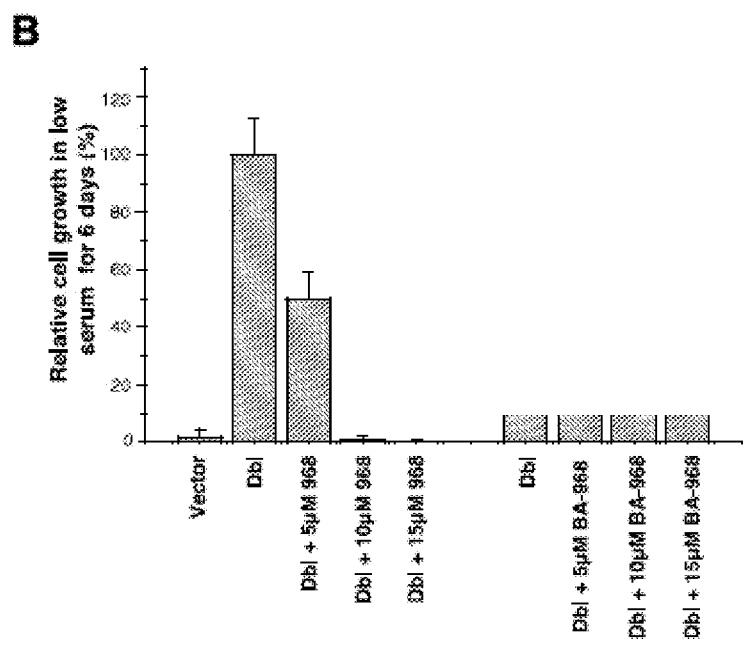
Figure 1D:
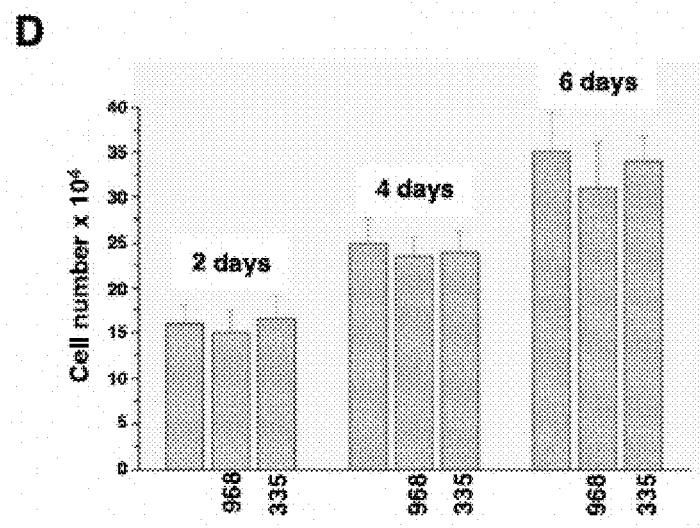
Figure 1E:
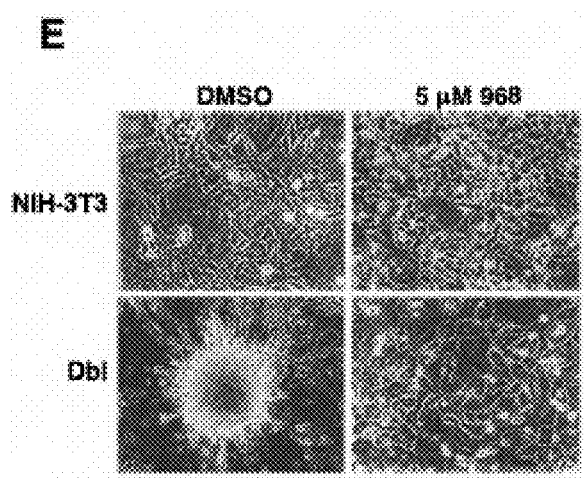

It is demonstrated here that members of the benzo[a]phenanthridinone family block the cellular transformation induced by the Rho family-GEF oncogenic Dbl (Diffuse B-cell lymphoma), as read-out in focus-forming assays or by growth in low serum (FIGS. 1A and 1B). The most effective molecule, designated 968, is active at 1-10 µM. The phenyl ring (circled in FIG. 1C) is essential for inhibitory activity, as the molecule designated BA-968 is still effective, albeit slightly less potent, in blocking Dbl-induced transformation. Compounds 335 or 384, which lack only the dimethyl amine or bromine, respectively, show little or no inhibition (FIGS. 1A and 5A). 968 is a more potent inhibitor of Dbl-induced transformation, compared to oncogenic H-Ras, when assaying focus formation in NIH 3T3 cells (FIGS. 5A and 5B), or growth in low serum (compare FIGS. 1B and 5C), indicating that the transforming activities of Rho GTPases are particularly sensitive to this small molecule. Treatment with 968 shows no significant effects on the growth or morphology of normal NIH 3T3 cells (FIGS. 1D and 1E).

Figure 2B:
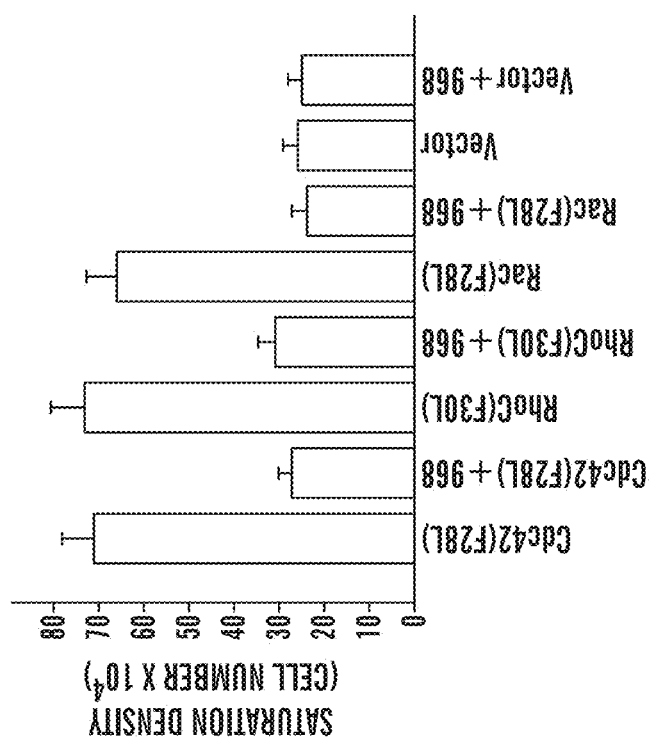
Figure 2A:
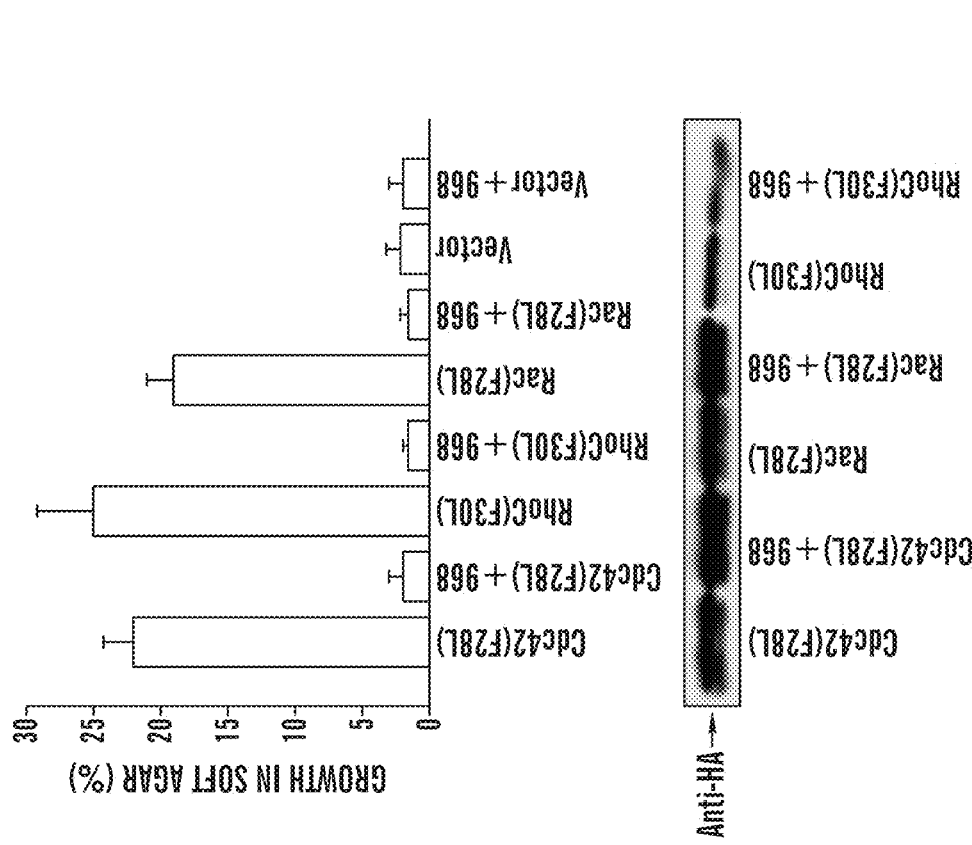

Mutated Rho GTPases that undergo constitutive GDP-GTP exchange ("fast-cyclers") mimic many of the actions of Dbl, enabling cells to grow in low serum, form colonies in soft-agar (i.e. anchorage-independent growth), and induce tumor formation when injected into immuno-compromised mice (Lin et al., "Specific Contributions of the Small GTPases Rho, Rac and Cdc42 to Dbl Transformation," *J. Biol. Chem.* 274:23633-23641 (1999), which is hereby incorporated by reference in its entirety). Cells transformed by different fast-cycling Rho GTPases were used to determine whether 968 blocked the signaling activity of a specific Rho GTPase-target of Dbl, such as RhoC. In fact, 968 inhibited the transforming activity of a number of activated Rho GTPase mutants, blocking their ability to stimulate NIH 3T3 cells to form colonies in soft-agar (FIG. 2A) and to grow to high density (FIG. 2B) or under low serum conditions (FIG. 2C), as well as inhibiting their invasive activity (FIG. 2D).

Figure 6:
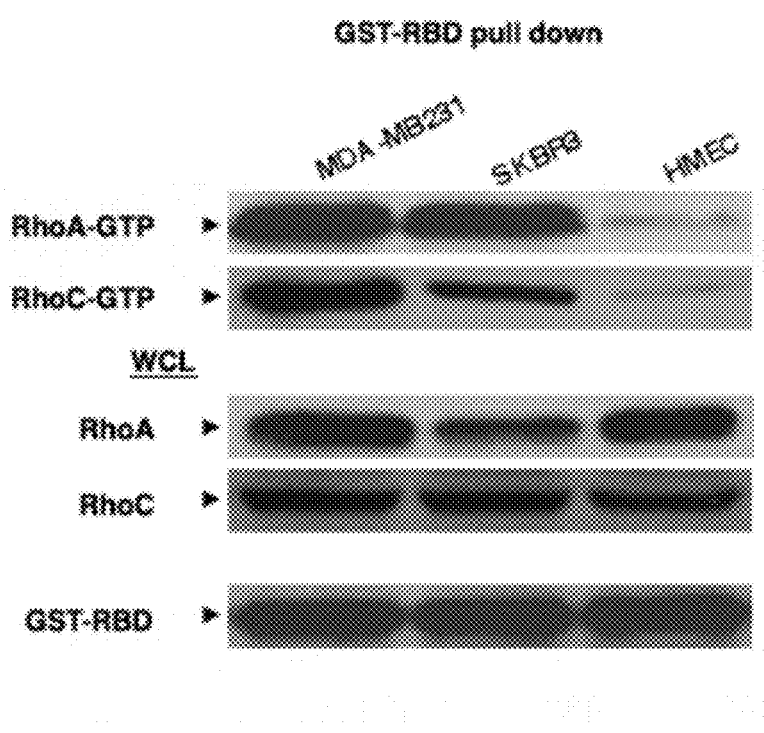
FIG. 6 shows that Rho GTPases are hyper-activated in breast cancer cells. Lysates from MDA-MB231 cells, SKBR3 cells, and HMECs, are prepared and incubated with GST fused to the limit Rho-binding domain on Rhotekin (GST-RBD). The top panels show the relative levels of RhoA-GTP and RhoC-GTP that are co-precipitated with GST-RBD from the indicated cells, as indicated by Western blotting with an anti-RhoA monoclonal antibody and an anti-RhoC polyclonal antibody. The middle panels compare the relative expression of RhoA and RhoC in whole cell lysates (WCL) from the different cells and the bottom panel shows the relative input of GST-RBD.

Rho GTPases have been implicated in human breast cancer (Burbelo et al., "Altered Rho GTPase Signaling Pathways in Breast Cancer Cells," *Breast Cancer Res. Treat.* 84:43-48 (2004); Valastyan et al., "A Pleiotropically Acting microRNA, miR-31, Inhibits Breast Cancer Metastasis," *Cell* 137:1032-1046 (2009), which are hereby incorporated by reference in their entirety). The highly invasive MDA-MB231 cells and SKBR3 cells represent two examples of breast cancer cell lines that exhibit hyper-activated RhoA and RhoC compared to normal human mammary epithelial cells (HMECs), as indicated in pull-down assays using GST fused to the Rho-binding domain of the effector protein Rhotekin (FIG. 6). Compound 968 inhibits the ability of both of these breast cancer cells to form colonies in soft agar, as effectively as it blocked Dbl-induced colony formation in NIH 3T3 cells (FIG. 2E). Similarly, 968 inhibits their growth to high density and in low serum, while having little effect on the growth of HMECs (FIGS. 2F and 2G).

Figure 3A:
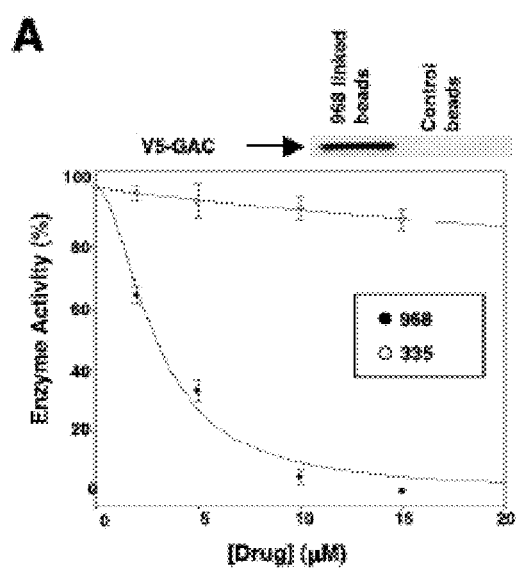
Figure 8:
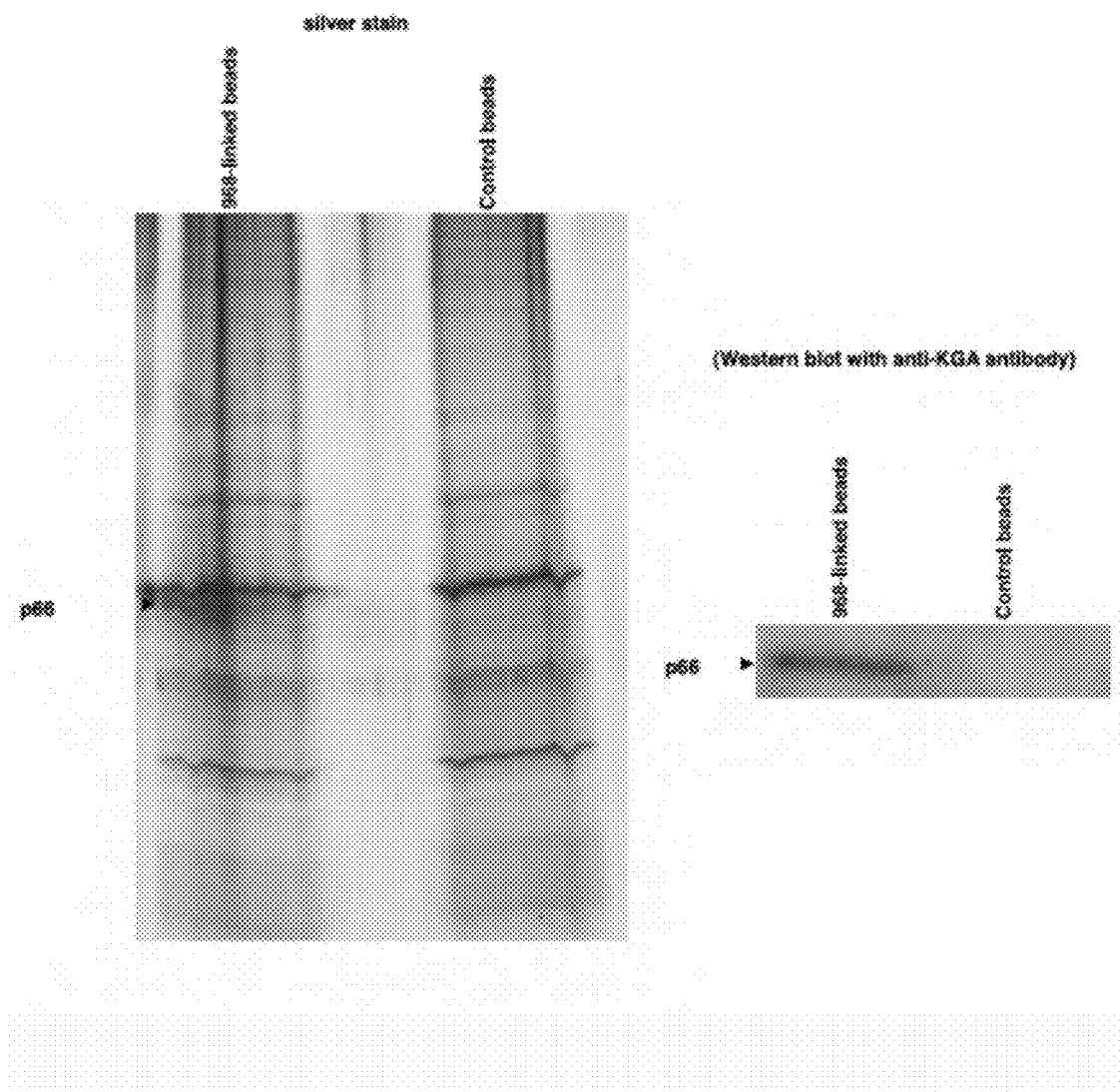
FIG. 8 illustrates that the biotin-labeled, active moiety of 968 binds to a 66 kDa protein that cross-reacts with the anti-KGA polyclonal antibody. The biotin-labeled, active moiety of 968 linked to streptavidin-agarose beads, or control beads alone, are incubated with lysates from NIH 3T3 cells stably expressing the constitutively active Cdc42 (F28L) mutant. Following precipitation of the beads and re-suspension, the samples are analyzed by SDS-PAGE and silver-staining (left-hand panel), as well as by Western blot analysis using an anti-KGA polyclonal antibody.
Figure 9:
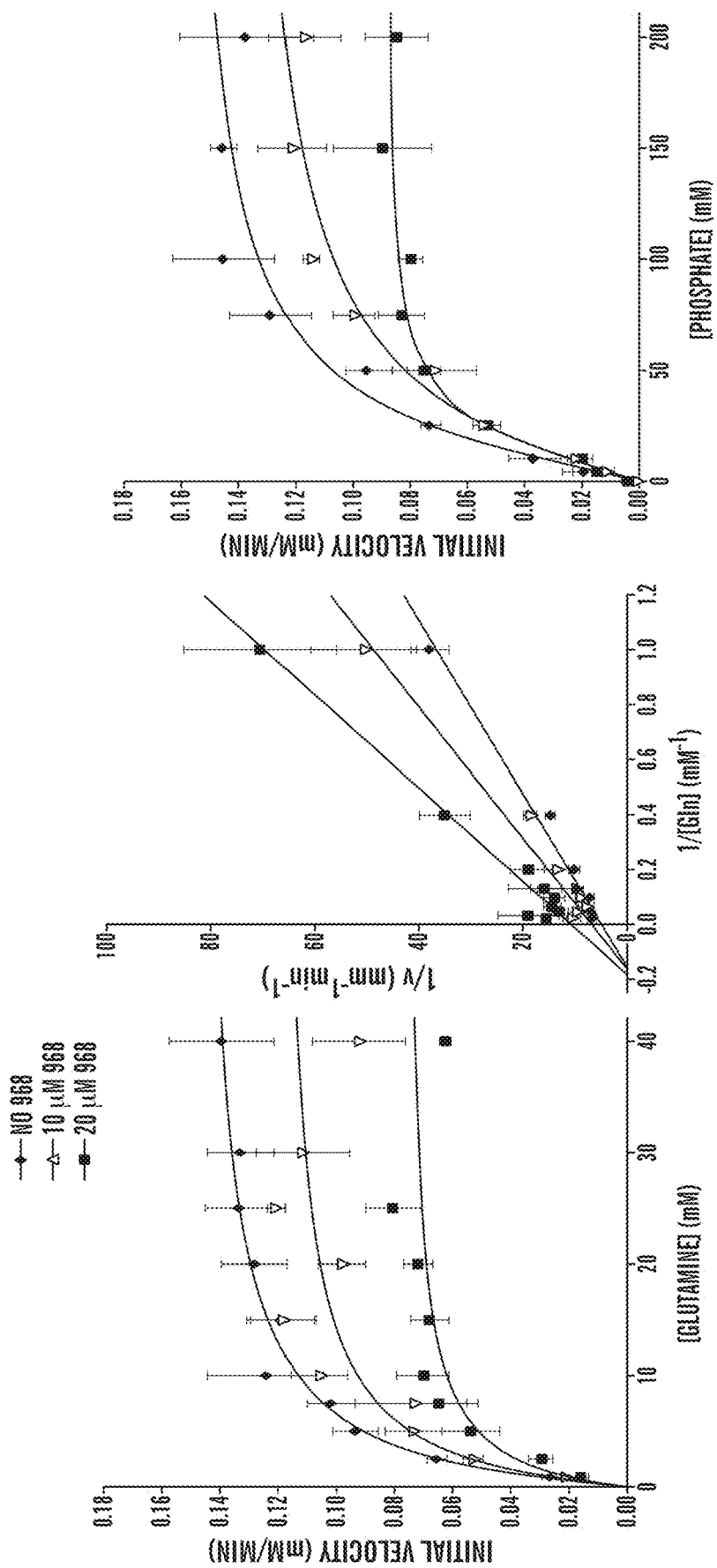
FIGS. 9A-C show that 968 is not competitive versus either the GA-substrate, glutamine, nor inorganic phosphate, an allosteric activator, of GA activity. The activity of the E. coli-expressed recombinant mouse ortholog of human GAC are assayed in the presence of 0 (●), 10 (▽) or 20 (■) μM 968 and inorganic phosphate in the form of dipotassium hydrogen phosphate.

The binding target for compound 968 can be identified by using the molecule active moiety (circled in FIG. 1C) labeled with biotin in affinity precipitation experiments with streptavidin beads. This experiment leads to the detection of a silver-stained band on SDS-gels, $M_r$~66 kDa, that can be isolated from Cdc42(F28L)-expressing NIH 3T3 cell lysates with the biotin-labeled 968-derivative immobilized to streptavidin beads, but not with beads alone. Microsequence analysis indicates that this 968-binding partner is the mouse isoform-2 ortholog of human glutaminase C (GAC), one of two splice variants of an enzyme found in kidney and other tissues, collectively referred to as kidney-type glutaminase (KGA), that catalyzes the hydrolysis of glutamine to glutamate and ammonium (Curthoys, N. P., "Regulation of Glutaminase Activity and Glutamine Metabolism," *Annu. Rev. Nutr.* 15:133-159 (1995), which is hereby incorporated by reference in its entirety) (FIG. 7). It has been verified that the biotin-labeled active moiety of 968, when immobilized on streptavidin beads, affinity-precipitates an endogenous protein of $M_r$~66 kDa that reacted with an antibody recognizing both isoforms of KGA (FIG. 8), as well as precipitated ectopically expressed VS-tagged GAC (FIG. 3A, top panel). Compound 968 inhibits the enzymatic activity of purified mouse GAC protein expressed in *E. coli*, whereas structurally-related compounds like 335 that are less effective at blocking Dbl-transformation (FIG. 1A), also showed little ability to inhibit enzyme activity (FIG. 3A). The inhibition by 968 is neither competitive versus substrate (glutamine) nor inorganic phosphate, an activator of the enzyme (Kenny et al., "Bacterial Expression, Purification and Characterization of Rat Kidney-Type Mitochondrial Glutaminase," *Protein Expr. Purif* 31:140-148 (2003), which is hereby incorporated by reference in its entirety), suggesting that it acts in an allosteric manner (FIGS. 9A-C).

Figure 3B:
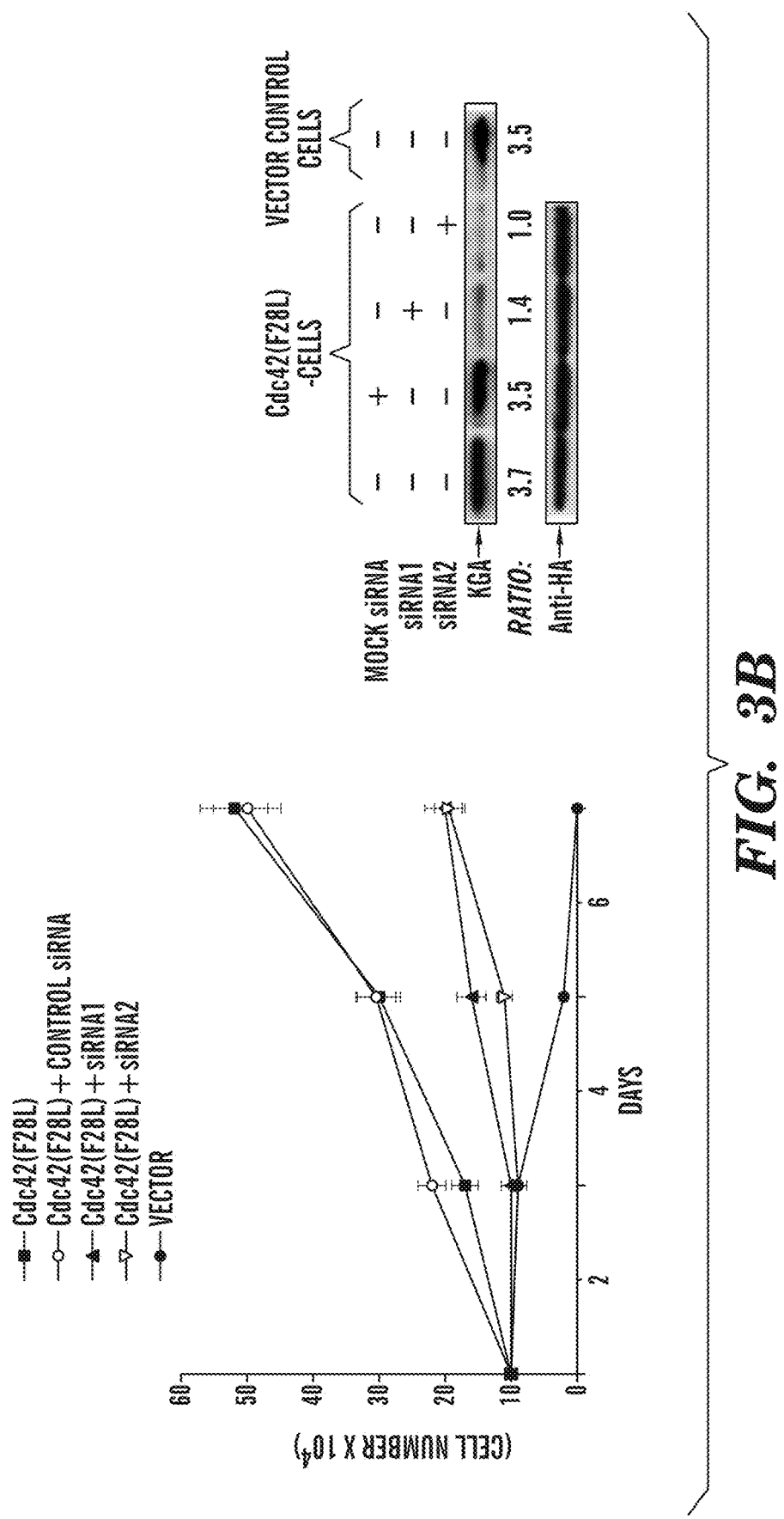
Figure 10:
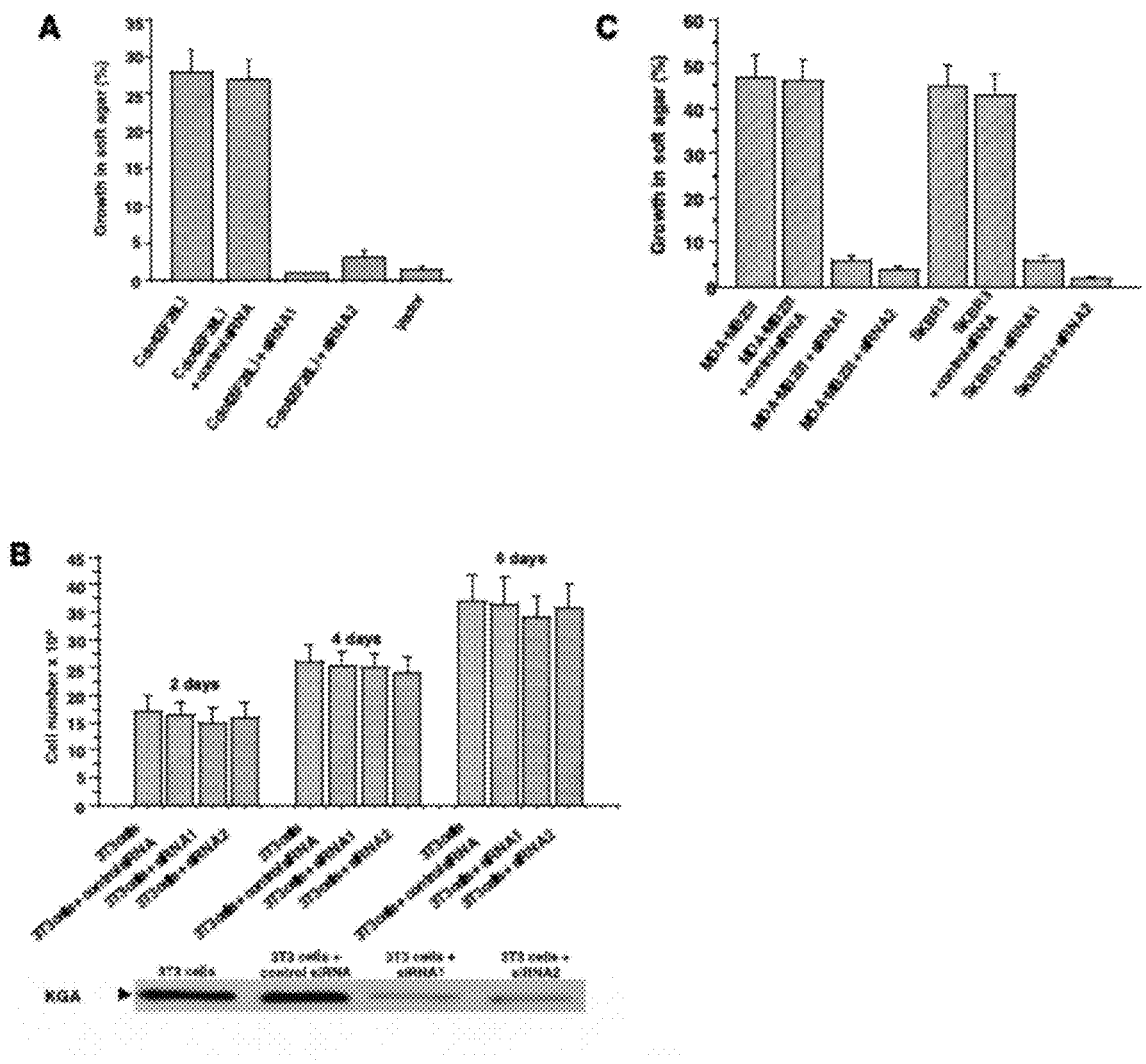
FIGS. 10A-C illustrate the effects of knocking-down KGA on the growth of transformed/cancer cells versus NIH 3T3 cells.

Reducing KGA expression by using siRNAs targeting both of its isoforms inhibits the ability of Cdc42(F28L) to stimulate growth in low serum (FIG. 3B) and colony formation in soft agar (FIG. 10A). Knocking-down KGA expression in control NIH 3T3 cells fails to significantly inhibit their growth in normal serum (FIG. 10B), consistent with the inability of 968 to affect their growth or overall morphology (FIGS. 1D and 1E), whereas it strongly inhibits MDA-MB231 and SKBR3 cells from growing in low serum (FIG. 3C) and in soft-agar (FIG. 10C). Because 968 blocks the growth of transformed/cancer cells by inhibiting glutaminase C activity, it should also eliminate the next step in glutamine metabolism, i.e., the generation of α-ketoglutarate from the GA-product glutamate. Moreover, this would predict that 968-inhibition can be circumvented by adding a cell-permeable analog of α-ketoglutarate to cells. Indeed, it was found to be the case in SKBR3 cells when assaying growth in low serum (FIG. 3D), as well as in Dbl-transformed cells when assaying focus-formation (FIG. 3E).

Dbl-transformed fibroblasts exhibit much higher basal GA activity (i.e. assayed in the absence of inorganic phosphate) than non-transformed NIH 3T3 cells (FIG. 3F). Cdc42(F28L)-expressing cells show basal levels of GA activity that are lower than those for Dbl-transformed cells, but still higher than non-transformed cells. The GA activity in control NIH 3T3 cells is strongly stimulated by phosphate (~6-fold), such that it approaches the maximum phosphate-stimulated activity obtained in transformed cells (FIG. 11A). Treatment of transformed cells with 968 inhibits their GA activity, with the basal activity being more sensitive than the phosphate-stimulated activity (see FIGS. 3F and 11A).

Both MDA-MB231 and SKBR3 cells show significantly higher basal GA activity, compared to normal HMECs, that is sensitive to 968 (FIG. 3G, top panel; the bottom panel shows that equivalent amounts of mitochondrial protein were assayed, by using the mitochondrial marker VDAC/Porin (Shimizu et al., "Bcl-2 Family Proteins Regulate the Release of Apoptogenic Cytochrome c by the Mitochondrial Channel VDAC," *Nature* 399:483-487 (1999), which is hereby incorporated by reference in its entirety)). Inorganic phosphate strongly stimulates the GA activity in HMECs (~5-fold), and although it is still lower than the maximum activity measured in MDA-MB231 cells, it is similar to the phosphate-stimulated activity assayed in SKBR3 cells (FIG. 11B). Knock-downs of RhoA and RhoC in SKBR3 cells markedly reduce their basal GA activity, without significantly affecting the direct stimulation of the enzyme by phosphate, indicating that the basal enzyme activity in these breast cancer cells is Rho GTPase-dependent (FIG. 11C).

The expression of GAC is shown to be significantly increased in B-lymphoma and prostate cancer cells and to be necessary for their proliferation and survival (Gao et al., "c-Myc Suppression of miR-23a/b Enhances Mitochondrial Glutaminase Expression and Glutamine Metabolism," Nature 458:762-765 (2009), which is hereby incorporated by reference in its entirety). The ectopic expression of GAC alone is insufficient to transform cells (FIG. 4A). However, the transient expression of GAC in cells stably expressing Cdc42(F28L) causes a dramatic increase in focus-forming activity, that matches Dbl-transformed cells which typically exhibit large numbers of foci and high basal levels of GA activity, and can be blocked by treatment with 968. When the catalytically dead GAC(S291A) mutant is co-expressed with Cdc42(F28L), there is no detectable increase in transforming activity compared to that for Cdc42(F28L) alone (FIG. 4B). Collectively, these findings demonstrate the need to reach a threshold level of GA activity to achieve the maximum transforming signal and that increased GAC expression alone is not sufficient for increased basal activity.

MDA-MB231 breast cancer cells show higher KGA expression compared to SKBR3 cells or normal HMECs when using an antibody which recognizes both enzyme isoforms (FIG. 3C, bottom panel; FIG. 3G, bottom panels), which likely accounts for their increased levels of basal (FIG. 3G, top panel) and phosphate-stimulated GA activity (FIG. 11B). However, significant differences in KGA expression in Dbl- or Cdc42(F28L)-transformed cells compared to control cells (FIG. 3F, bottom panel) have not been detected, consistent with their showing similar levels of phosphate-stimulated GA activity (FIG. 11A). Likewise, KGA expression in SKBR3 cells is not significantly different from normal HMECs (FIG. 3G, bottom panels), as born out by their similar levels of phosphate-stimulated GA activity (FIG. 11B). Therefore, the increase in basal GA activity in SKBR3 cells, as well as in Dbl- and Rho GTPase-transformed fibroblasts, cannot be simply attributed to an up-regulation of enzyme expression.

A clue regarding how GA is activated in these transformed/cancer cells came from the finding that the treatment of Dbl-transformed cells and SKBR3 breast cancer cells with BAY 11-7082, which blocks NF-kB activation by inhibiting the upstream kinase IKKb (Pickering et al., "Pharmacological Inhibitors of NF-κB Accelerate Apoptosis in Chronic Lymphocytic Leukemia Cells," Oncogene 26:1166-1177 (2007), which is hereby incorporated by reference in its entirety), significantly reduces their basal GA activity (FIGS. 4C and 4D, respectively). NF-κB is activated by Dbl and various Rho GTPases (Perona et al., "Activation of the Nuclear Factor-κB by Rho, CDC42, and Rac-1 Proteins," Genes Dev. 11:463-475 (1997); Joyce et al., "Integration of Rac-Dependent Regulation of cyclin D1 Transcription Through a Nuclear Factor-KB-Dependent Pathway," J. Biol. Chem. 274:25245-25249 (1999); Cammarano et al., "Dbl and the Rho GTPases Activate NFκB by IκB kinase (IKK)-Dependent and IKK-Independent Pathways," J. Biol. Chem. 276:25876-25882 (2001), which are hereby incorporated by reference in their entirety), and is essential for Dbl-transformation (Whitehead et al., "Dependence of Dbl and Dbs Transformation on MEK and NF-kappaB Activation," Mol. Cell Biol. 19:7759-7770 (1999), which is hereby incorporated by reference in its entirety) and for the transformed phenotypes of human breast cancer cells (Sovak et al., "Aberrant Nuclear Factor-kB/Rel Expression and the Pathogenesis of Breast Cancer," J. Clin. Invest. 100:2952-2960 (1997), which is hereby incorporated by reference in its entirety). Knocking-down the p65/RelA subunit of NF-kB in Dbl-transformed cells and SKBR3 cells also markedly reduces their basal GA activity (FIGS. 4C and 4D), whereas treatment with BAY 11-7082 or knock-downs of p65/RelA has little or no effect on the direct stimulation of the enzyme by phosphate (Figures S7D and 11E).

NF-kB might regulate GA by inducing the expression of a protein that stimulates its activity through a direct interaction or via a post-translational modification. The latter would be analogous to how the tyrosine phosphorylation of the M2 isoform of pyruvate kinase has been suggested to influence glycolysis in cancer cells (Christofk et al., "Pyruvate Kinase M2 is a Phosphotyrosine-Binding Protein," Nature 452:181-186 (2008), which is hereby incorporated by reference in its entirety). Indeed, it has been found that V5-tagged GAC, when ectopically expressed in Dbl-transformed cells followed by its immunoprecipitation (IP), exhibits significantly higher activity compared to V5-GAC IPed from non-transformed NIH 3T3 cells (FIG. 4E). The GA activity IPed from Dbl-transformed cells is inhibited by both 968 and BA-968, and is markedly reduced when NF-kB activation is blocked prior to IP, thus consistent with the suggestion that GAC is modified in transformed cells in an NF-kB-dependent manner.

The importance of cellular metabolism in the development of cancer, and in particular, the early observations that tumor cells exhibit enhanced glycolytic activity (i.e. the "Warburg effect"), are receiving renewed attention (DeBerardinis et al., "Beyond Aerobic Glycolysis: Transformed Cells Can Engage in Glutamine Metabolism that Exceeds the Requirement for Protein and Nucleotide Synthesis," Proc. Natl. Acad. Sci. USA 104:19345-19350 (2007); Christofk et al., "Pyruvate Kinase M2 is a Phosphotyrosine-Binding Protein," Nature 452:181-186 (2008), which are hereby incorporated by reference in their entirety). $^{13}$C-NMR metabolic flux experiments have demonstrated that while proliferating cancer cells exhibit a pronounced Warburg effect, their TCA cycle remains intact and is driven by glutamine metabolism (DeBerardinis et al., "Beyond Aerobic Glycolysis: Transformed Cells Can Engage in Glutamine Metabolism that Exceeds the Requirement for Protein and Nucleotide Synthesis," Proc. Natl. Acad. Sci. USA 104: 19345-19350 (2007), which is hereby incorporated by reference in its entirety). This enables cancer cells to supply a significant fraction of TCA cycle intermediates as precursors for biosynthetic pathways (DeBerardinis et al., "The Biology of Cancer: Metabolic Reprogramming Fuels Cell Growth and Proliferation," Cell Metab. 7:11-19 (2008), which is hereby incorporated by reference in its entirety), and is consistent with the observations that tumor cells exhibit increased rates of glutamine metabolism and consume greater amounts of glutamine compared to normal cells (Medina et al., "Relevance of Glutamine Metabolism to Tumor Cell Growth," Mol. Cell. Biochem. 113:1-15 (1992), which is hereby incorporated by reference in its entirety). The observation that different transformed cell lines and cancer cells show elevated GA activity in their mitochondria that is dependent on Rho GTPase/NF-kB-signaling provides a mechanism for how these demands for elevated glutamine metabolism are met. Moreover, the ability of the small molecule 968 to inhibit GA activity and influence the aberrant growth properties of transformed/cancer cells raises intriguing possibilities for new strategies of therapeutic intervention against cancer.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating a subject with a condition mediated by production of glutamate from glutamine by glutaminase C, said method comprising:

selecting a subject with a condition mediated by production of glutamate from glutamine by glutaminase C, wherein the condition is breast cancer; and administering to said selected subject an inhibitor of glutaminase C activity under conditions effective to treat said breast cancer, wherein the inhibitor is a compound of Formula I:

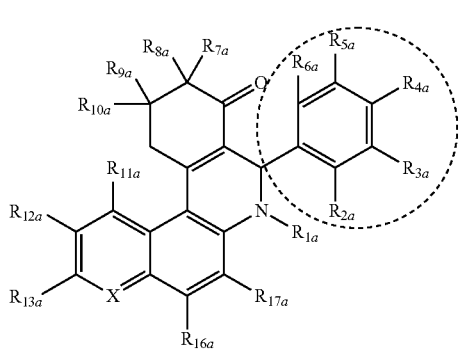

wherein:
the dotted circle identifies an active moiety;
X is independently —$CR_{14a}$— or N;
$R_{1a}$ is independently H, OH, $OR_{14a}$, $C_1$-$C_6$ alkyl, $C_2$-$C_6$ alkenyl, $C_2$-$C_6$ alkynyl, $R_{14a}C(O)$—, $R_{14a}OC(O)$—, $R_{14a}S(O)$—, or $R_{14a}S(O)_2$—;
$R_{2a}$, $R_{3a}$, $R_{4a}$, $R_{5a}$, and $R_{6a}$ are each independently H, halogen, $NO_2$, OH, $OR_{14a}$, —$SR_{14a}$, $NH_2$, $NHR_{14a}$, $NR_{14a}R_{15a}$, $R_{14a}C(O)$—, $R_{14a}OC(O)$—, $R_{14a}C(O)O$—, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen; or $R_{2a}$ and $R_{3a}$, $R_{3a}$ and $R_{4a}$, $R_{4a}$ and $R_{5a}$, or $R_{5a}$ and $R_{6a}$ can combine to form a heterocyclic ring;

$R_{7a}$, $R_{8a}$, $R_{9a}$, and $R_{10a}$ are each independently H, OH, $NH_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl with each cyclic unit containing from 1 to 5 heteroatoms selected from the group consisting of nitrogen, sulfur, and oxygen, wherein the aryl, heteroaryl, and aryl $C_1$-$C_6$ alkyl are optionally substituted from 1 to 3 times with substituents selected from the group consisting of halogen, OH, $NH_2$, $C_1$-$C_6$ alkyl, $C_2$-$C_6$ alkenyl, $C_1$-$C_6$ alkoxy, SH, and $C_1$-$C_6$thioalkyl; and $R_{11a}$, $R_{12a}$, $R_{13a}$, $R_{14a}$, $R_{15a}$, $R_{16a}$, and $R_{17a}$ are each independently H, halogen, OH, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, each one of $R_{11a}$-$R_{17a}$ optionally substituted with $NH_2$, OH, halogen, COOH, $NO_2$ and CN.

2. The method of claim 1, wherein the inhibitor inhibits phosphorylation of glutaminase C.

3. The method of claim 1, wherein the inhibitor inhibits expression-independent glutaminase C activity and/or glutaminase C activity independent of exogenous phosphate addition.

4. The method of claim 1, wherein the compound comprises an active moiety of formula:

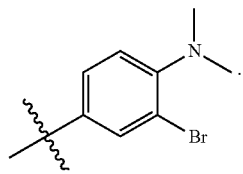 [SMILES: *c1ccc(N(C)C)c(Br)c1]

5. The method of claim 1, wherein said administering is performed parenterally, orally, subcutaneously, intravenously, intramuscularly, extraperitoneally, by intranasal instillation, or by application to mucous membranes.

* * * * *